United States Patent [19]
Dow et al.

[11] Patent Number: 5,705,151
[45] Date of Patent: Jan. 6, 1998

[54] GENE THERAPY FOR T CELL REGULATION

[75] Inventors: Steve W. Dow; Robyn E. Elmslie, both of Denver, Colo.

[73] Assignee: National Jewish Center for Immunology & Respiratory Medicine, Denver, Colo.

[21] Appl. No.: 446,918

[22] Filed: May 18, 1995

[51] Int. Cl.$^6$ .................. A61K 48/00; C12N 15/63; C12N 15/09; C12N 5/00

[52] U.S. Cl. .................. 424/93.21; 424/450; 514/44; 435/69.1; 435/172.3; 435/7.2; 435/320.1; 935/62; 935/55; 935/54; 935/71

[58] Field of Search .................. 514/44; 435/320.1, 435/240.2, 6, 7.1, 69.1, 172.3, 69.5 T, 7.2; 935/62, 52, 55, 56, 57, 32, 54, 66, 70, 71, 33, 34, 72, 65; 424/93.1, 93.2 T, 130.1, 450; 536/23 T

[56] References Cited

FOREIGN PATENT DOCUMENTS

WO 95/00178  1/1995  WIPO.

OTHER PUBLICATIONS

Blackman et al., *Life Sci.*, 57(19):1717–1735, 1995.
Donnelly et al., *Ann. N.Y. Acad. Sci.*, 772:40–46, 1995.
Liu, *Ann. N.Y. Acad. Sci.*, 772(DNA Vaccines):15–21, 1995.
Miethke et al., *Int. Arch. Allergy Immunol.*, 106:3–7, 1995.
Miethke et al., *Immunobiol.*, 189:270–284, 1993.
Liu et al., 1997, *Nature Biotechnology*, 15:167–173.

*Primary Examiner*—Jasemine C. Chambers
*Assistant Examiner*—Karen M. Hauda
*Attorney, Agent, or Firm*—Sheridan Ross P.C.

[57] ABSTRACT

The present invention provides a nucleic acid-based therapeutic composition to treat an animal with disease by controlling the activity of effector cells, including T cells, macrophages, monocytes and/or natural killer cells, in the animal. The present invention also relates to methods of gene therapy involving different modes of administration of a therapeutic composition to treat animals with different types of diseases. Also included in the present invention are recombinant molecules for use in a therapeutic composition and recombinant cells useful as a tumor vaccine. Therapeutic compositions of the present invention include superantigen-encoding nucleic acid molecules, either in the presence or absence of a cytokine-encoding nucleic acid molecule, depending upon the disease being treated.

52 Claims, 10 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 773 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 1..768

( x i ) SEQUENCE DESCRIPTION: SEQ ID NO:1:

```
ATG  ACC  ATG  ATT  ACG  AAT  TTA  ATA  CGA  CTC  ACT  ATA  GGG  AAT  TCC  ATG         48
Met  Thr  Met  Ile  Thr  Asn  Leu  Ile  Arg  Leu  Thr  Ile  Gly  Asn  Ser  Met
 1              5                        10                       15

GAG  AGT  CAA  CCA  GAT  CCT  AAA  CCA  GAT  GAG  TTG  CAC  AAA  TCG  AGT  AAA         96
Glu  Ser  Gln  Pro  Asp  Pro  Lys  Pro  Asp  Glu  Leu  His  Lys  Ser  Ser  Lys
              20                       25                       30

TTC  ACT  GGT  TTG  ATG  GAA  AAT  ATG  AAA  GTT  TTG  TAT  GAT  GAT  AAT  CAT        144
Phe  Thr  Gly  Leu  Met  Glu  Asn  Met  Lys  Val  Leu  Tyr  Asp  Asp  Asn  His
         35                       40                       45

GTA  TCA  GCA  ATA  AAC  GTT  AAA  TCT  ATA  GAT  CAA  TTT  CTA  TAC  TTT  GAC        192
Val  Ser  Ala  Ile  Asn  Val  Lys  Ser  Ile  Asp  Gln  Phe  Leu  Tyr  Phe  Asp
     50                       55                       60

TTA  ATA  TAT  TCT  ATT  AAG  GAC  ACT  AAG  TTA  GGG  AAT  TAT  GAT  AAT  GTT        240
Leu  Ile  Tyr  Ser  Ile  Lys  Asp  Thr  Lys  Leu  Gly  Asn  Tyr  Asp  Asn  Val
 65                       70                       75                       80

CGA  GTC  GAA  TTT  AAA  AAC  AAA  GAT  TTA  GCT  GAT  AAA  TAC  AAA  GAT  AAA        288
Arg  Val  Glu  Phe  Lys  Asn  Lys  Asp  Leu  Ala  Asp  Lys  Tyr  Lys  Asp  Lys
                  85                       90                       95
```

| | | | | | | | | | | | | | | | | |
|---|---|---|---|---|---|---|---|---|---|---|---|---|---|---|---|---|
| TAC | GTA | GAT | GTG | TTT | GGA | GCT | AAT | TAT | TAT | TAT | CAA | TGT | TAT | TTT | TCT | 336 |
| Tyr | Val | Asp | Val | Phe | Gly | Ala | Asn | Tyr | Tyr | Tyr | Gln | Cys | Tyr | Phe | Ser | |
| | | | 100 | | | | | 105 | | | | | 110 | | | |
| AAA | AAA | ACG | AAT | GAT | ATT | AAT | TCG | CAT | CAA | ACT | GAC | AAA | CGA | AAA | ACT | 384 |
| Lys | Lys | Thr | Asn | Asp | Ile | Asn | Ser | His | Gln | Thr | Asp | Lys | Arg | Lys | Thr | |
| | | 115 | | | | | 120 | | | | | 125 | | | | |
| TGT | ATG | TAT | GGT | GGT | GTA | ACT | GAG | CAT | AAT | GGA | AAC | CAA | TTA | GAT | AAA | 432 |
| Cys | Met | Tyr | Gly | Gly | Val | Thr | Glu | His | Asn | Gly | Asn | Gln | Leu | Asp | Lys | |
| | 130 | | | | | 135 | | | | | 140 | | | | | |
| TAT | AGA | AGT | ATT | ACT | GTT | CGG | GTA | TTT | GAA | GAT | GGT | AAA | AAT | TTA | TTA | 480 |
| Tyr | Arg | Ser | Ile | Thr | Val | Arg | Val | Phe | Glu | Asp | Gly | Lys | Asn | Leu | Leu | |
| 145 | | | | | 150 | | | | | 155 | | | | | 160 | |
| TCT | TTT | GAC | GTA | CAA | ACT | AAT | AAG | AAA | AAG | GTG | ACT | GCT | CAA | GAA | TTA | 528 |
| Ser | Phe | Asp | Val | Gln | Thr | Asn | Lys | Lys | Lys | Val | Thr | Ala | Gln | Glu | Leu | |
| | | | | 165 | | | | | 170 | | | | | 175 | | |
| GAT | TAC | CTA | ACT | CGT | CAC | TAT | TTG | GTG | AAA | AAT | AAA | AAA | CTC | TAT | GAA | 576 |
| Asp | Tyr | Leu | Thr | Arg | His | Tyr | Leu | Val | Lys | Asn | Lys | Lys | Leu | Tyr | Glu | |
| | | | 180 | | | | | 185 | | | | | 190 | | | |
| TTT | AAC | AAC | TCG | CCT | TAT | GAA | ACG | GGA | TAT | ATT | AAA | TTT | ATA | GAA | AAT | 624 |
| Phe | Asn | Asn | Ser | Pro | Tyr | Glu | Thr | Gly | Tyr | Ile | Lys | Phe | Ile | Glu | Asn | |
| | | 195 | | | | | 200 | | | | | 205 | | | | |
| GAG | AAT | AGC | TTT | TGG | TAT | GAC | ATG | ATG | CCT | GCA | CCA | GGA | GAT | AAA | TTT | 672 |
| Glu | Asn | Ser | Phe | Trp | Tyr | Asp | Met | Met | Pro | Ala | Pro | Gly | Asp | Lys | Phe | |
| | 210 | | | | | 215 | | | | | 220 | | | | | |
| GAC | CAA | TCT | AAA | TAT | TTA | ATG | ATG | TAC | AAT | GAC | AAT | AAA | ATG | GTT | GAT | 720 |
| Asp | Gln | Ser | Lys | Tyr | Leu | Met | Met | Tyr | Asn | Asp | Asn | Lys | Met | Val | Asp | |
| 225 | | | | | 230 | | | | | 235 | | | | | 240 | |
| TCT | AAA | GAT | GTG | AAG | ATT | GAA | GTT | TAT | CTT | ACG | ACA | AAG | AAA | AAG | TGAAGCTT | 773 |
| Ser | Lys | Asp | Val | Lys | Ile | Glu | Val | Tyr | Leu | Thr | Thr | Lys | Lys | Lys | | |
| | | | | 245 | | | | | 250 | | | | | 255 | | |

( 2 ) INFORMATION FOR SEQ ID NO:2:

( i ) SEQUENCE CHARACTERISTICS:
        ( A ) LENGTH: 255 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Thr | Met | Ile | Thr | Asn | Leu | Ile | Arg | Leu | Thr | Ile | Gly | Asn | Ser | Met |
| 1 | | | | 5 | | | | | 10 | | | | | 15 | |
| Glu | Ser | Gln | Pro | Asp | Pro | Lys | Pro | Asp | Glu | Leu | His | Lys | Ser | Ser | Lys |
| | | | 20 | | | | | 25 | | | | | 30 | | |
| Phe | Thr | Gly | Leu | Met | Glu | Asn | Met | Lys | Val | Leu | Tyr | Asp | Asp | Asn | His |
| | | 35 | | | | | 40 | | | | | 45 | | | |
| Val | Ser | Ala | Ile | Asn | Val | Lys | Ser | Ile | Asp | Gln | Phe | Leu | Tyr | Phe | Asp |
| | 50 | | | | | 55 | | | | | 60 | | | | |
| Leu | Ile | Tyr | Ser | Ile | Lys | Asp | Thr | Lys | Leu | Gly | Asn | Tyr | Asp | Asn | Val |
| 65 | | | | | 70 | | | | | 75 | | | | | 80 |
| Arg | Val | Glu | Phe | Lys | Asn | Lys | Asp | Leu | Ala | Asp | Lys | Tyr | Lys | Asp | Lys |
| | | | | 85 | | | | | 90 | | | | | 95 | |
| Tyr | Val | Asp | Val | Phe | Gly | Ala | Asn | Tyr | Tyr | Tyr | Gln | Cys | Tyr | Phe | Ser |
| | | | 100 | | | | | 105 | | | | | 110 | | |
| Lys | Lys | Thr | Asn | Asp | Ile | Asn | Ser | His | Gln | Thr | Asp | Lys | Arg | Lys | Thr |
| | | 115 | | | | | 120 | | | | | 125 | | | |
| Cys | Met | Tyr | Gly | Gly | Val | Thr | Glu | His | Asn | Gly | Asn | Gln | Leu | Asp | Lys |
| | 130 | | | | | 135 | | | | | 140 | | | | |

-continued

```
Tyr Arg Ser Ile Thr Val Arg Val Phe Glu Asp Gly Lys Asn Leu Leu
145                 150                 155                 160

Ser Phe Asp Val Gln Thr Asn Lys Lys Val Thr Ala Gln Glu Leu
                165                 170             175

Asp Tyr Leu Thr Arg His Tyr Leu Val Lys Asn Lys Lys Leu Tyr Glu
            180                 185                 190

Phe Asn Asn Ser Pro Tyr Glu Thr Gly Tyr Ile Lys Phe Ile Glu Asn
        195                 200                 205

Glu Asn Ser Phe Trp Tyr Asp Met Met Pro Ala Pro Gly Asp Lys Phe
    210                 215                 220

Asp Gln Ser Lys Tyr Leu Met Met Tyr Asn Asp Asn Lys Met Val Asp
225                 230                 235                 240

Ser Lys Asp Val Lys Ile Glu Val Tyr Leu Thr Thr Lys Lys Lys
                245                 250                 255
```

( 2 ) INFORMATION FOR SEQ ID NO:3:

( i ) SEQUENCE CHARACTERISTICS:
    ( A ) LENGTH: 751 base pairs
    ( B ) TYPE: nucleic acid
    ( C ) STRANDEDNESS: single
    ( D ) TOPOLOGY: linear ( i i ) MOLECULE TYPE: protein ( i x ) FEATURE:
    ( A ) NAME/KEY: CDS
    ( B ) LOCATION: 46..747

( x i ) SEQUENCE DESCRIPTION: SEQ ID NO:3:

```
ATGACCATGA TTACGAATTT AATACGACTC ACTATAGGGA ATTCC ATG GAG AAA           54
                                                  Met Glu Lys
                                                   1

AGC GAA GAA ATA AAT GAG AAA GAT CTG CGC AAG AAG TCC GAA TTG CAG       102
Ser Glu Glu Ile Asn Glu Lys Asp Leu Arg Lys Lys Ser Glu Leu Gln
     5              10                  15

GGA ACA GCC CTA GGC AAT CTT AAA CAA ATC TAT TAT TAC AAT GAA AAA       150
Gly Thr Ala Leu Gly Asn Leu Lys Gln Ile Tyr Tyr Tyr Asn Glu Lys
 20                  25                  30                  35

GCG AAG ACT GAG AAT AAA GAG AGT CAC GAT CAA TTT CTG CAG CAT ACT       198
Ala Lys Thr Glu Asn Lys Glu Ser His Asp Gln Phe Leu Gln His Thr
             40                  45                  50

ATA TTG TTT AAA GGC TTT TTT ACT GAT CAT TCG TGG TAT AAC GAT TTA       246
Ile Leu Phe Lys Gly Phe Phe Thr Asp His Ser Trp Tyr Asn Asp Leu
         55                  60                  65

CTA GTA GAT TTT GAT TCG AAG GAC ATC GTT GAT AAA TAT AAA GGG AAG       294
Leu Val Asp Phe Asp Ser Lys Asp Ile Val Asp Lys Tyr Lys Gly Lys
     70                  75                  80

AAG GTC GAC TTG TAT GGT GCT TAT TAT GGG TAC CAA TGT GCT GGT GGT       342
Lys Val Asp Leu Tyr Gly Ala Tyr Tyr Gly Tyr Gln Cys Ala Gly Gly
 85                  90                  95

ACA CCA AAC AAA ACA GCA TGC ATG TAT GGT GGG GTA ACC TTA CAT GAC       390
Thr Pro Asn Lys Thr Ala Cys Met Tyr Gly Gly Val Thr Leu His Asp
100                 105                 110                 115

AAT AAT CGA TTG ACC GAA GAG AAA AAG GTC CCG ATC AAT TTA TGG CTA       438
Asn Asn Arg Leu Thr Glu Glu Lys Lys Val Pro Ile Asn Leu Trp Leu
            120                 125                 130

GAC GGT AAA CAA AAT ACA GTA CCT CTA GAA ACG GTT AAA ACG AAT AAG       486
Asp Gly Lys Gln Asn Thr Val Pro Leu Glu Thr Val Lys Thr Asn Lys
        135                 140                 145

AAA AAT GTA ACT GTC CAA GAG CTG GAT CTT CAA GCG CGC CGA TAC CTA       534
Lys Asn Val Thr Val Gln Glu Leu Asp Leu Gln Ala Arg Arg Tyr Leu
```

|     |     |     |     |     |     |     |     |     |     |     |     |     |     |     |     |
|-----|-----|-----|-----|-----|-----|-----|-----|-----|-----|-----|-----|-----|-----|-----|-----|
| | | | 150 | | | | | 155 | | | | | 160 | | |
| CAG | GAA | AAA | TAT | AAT | TTG | TAC | AAC | TCT | GAC | GTC | TTT | GAT | GGG | AAG | GTT | 582
| Gln | Glu | Lys | Tyr | Asn | Leu | Tyr | Asn | Ser | Asp | Val | Phe | Asp | Gly | Lys | Val |
| | 165 | | | | 170 | | | | | 175 | | | | | |
| CAG | AGA | GGC | CTA | ATC | GTG | TTT | CAT | ACT | TCT | ACA | GAA | CCT | TCG | GTT | AAC | 630
| Gln | Arg | Gly | Leu | Ile | Val | Phe | His | Thr | Ser | Thr | Glu | Pro | Ser | Val | Asn |
| 180 | | | | | 185 | | | | | 190 | | | | | 195 |
| TAC | GAT | TTA | TTT | GGA | GCT | CAA | GGA | CAG | TAT | TCA | AAT | ACA | CTC | TTA | AGA | 678
| Tyr | Asp | Leu | Phe | Gly | Ala | Gln | Gly | Gln | Tyr | Ser | Asn | Thr | Leu | Leu | Arg |
| | | | | 200 | | | | | 205 | | | | | 210 | |
| ATA | TAT | CGC | GAC | AAC | AAG | ACG | ATT | AAC | TCT | GAA | AAC | ATG | CAC | ATT | GAT | 726
| Ile | Tyr | Arg | Asp | Asn | Lys | Thr | Ile | Asn | Ser | Glu | Asn | Met | His | Ile | Asp |
| | | | 215 | | | | | 220 | | | | | 225 | | |
| ATC | TAT | TTA | TAT | ACA | AGT | TAAGCTT | | | | | | | | | | 751
| Ile | Tyr | Leu | Tyr | Thr | Ser | | | | | | | | | | |
| | | 230 | | | | | | | | | | | | | |

( 2 ) INFORMATION FOR SEQ ID NO:4:

( i ) SEQUENCE CHARACTERISTICS:
        ( A ) LENGTH: 233 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

|     |     |     |     |     |     |     |     |     |     |     |     |     |     |     |
|-----|-----|-----|-----|-----|-----|-----|-----|-----|-----|-----|-----|-----|-----|-----|
| Met | Glu | Lys | Ser | Glu | Glu | Ile | Asn | Glu | Lys | Asp | Leu | Arg | Lys | Lys | Ser |
| 1 | | | | 5 | | | | | 10 | | | | | 15 | |
| Glu | Leu | Gln | Gly | Thr | Ala | Leu | Gly | Asn | Leu | Lys | Gln | Ile | Tyr | Tyr | Tyr |
| | | | 20 | | | | | 25 | | | | | 30 | | |
| Asn | Glu | Lys | Ala | Lys | Thr | Glu | Asn | Lys | Glu | Ser | His | Asp | Gln | Phe | Leu |
| | | 35 | | | | | 40 | | | | | 45 | | | |
| Gln | His | Thr | Ile | Leu | Phe | Lys | Gly | Phe | Phe | Thr | Asp | His | Ser | Trp | Tyr |
| | 50 | | | | | 55 | | | | | 60 | | | | |
| Asn | Asp | Leu | Leu | Val | Asp | Phe | Asp | Ser | Lys | Asp | Ile | Val | Asp | Lys | Tyr |
| 65 | | | | | 70 | | | | | 75 | | | | | 80 |
| Lys | Gly | Lys | Lys | Val | Asp | Leu | Tyr | Gly | Ala | Tyr | Tyr | Gly | Tyr | Gln | Cys |
| | | | | 85 | | | | | 90 | | | | | 95 | |
| Ala | Gly | Gly | Thr | Pro | Asn | Lys | Thr | Ala | Cys | Met | Tyr | Gly | Gly | Val | Thr |
| | | | 100 | | | | | 105 | | | | | 110 | | |
| Leu | His | Asp | Asn | Asn | Arg | Leu | Thr | Glu | Glu | Lys | Lys | Val | Pro | Ile | Asn |
| | | 115 | | | | | 120 | | | | | 125 | | | |
| Leu | Trp | Leu | Asp | Gly | Lys | Gln | Asn | Thr | Val | Pro | Leu | Glu | Thr | Val | Lys |
| | 130 | | | | | 135 | | | | | 140 | | | | |
| Thr | Asn | Lys | Lys | Asn | Val | Thr | Val | Gln | Glu | Leu | Asp | Leu | Gln | Ala | Arg |
| 145 | | | | | 150 | | | | | 155 | | | | | 160 |
| Arg | Tyr | Leu | Gln | Glu | Lys | Tyr | Asn | Leu | Tyr | Asn | Ser | Asp | Val | Phe | Asp |
| | | | | 165 | | | | | 170 | | | | | 175 | |
| Gly | Lys | Val | Gln | Arg | Gly | Leu | Ile | Val | Phe | His | Thr | Ser | Thr | Glu | Pro |
| | | | 180 | | | | | 185 | | | | | 190 | | |
| Ser | Val | Asn | Tyr | Asp | Leu | Phe | Gly | Ala | Gln | Gly | Gln | Tyr | Ser | Asn | Thr |
| | | 195 | | | | | 200 | | | | | 205 | | | |
| Leu | Leu | Arg | Ile | Tyr | Arg | Asp | Asn | Lys | Thr | Ile | Asn | Ser | Glu | Asn | Met |
| | 210 | | | | | 215 | | | | | 220 | | | | |
| His | Ile | Asp | Ile | Tyr | Leu | Tyr | Thr | Ser | | | | | | | |
| 225 | | | | | 230 | | | | | | | | | | |

( 2 ) INFORMATION FOR SEQ ID NO:5:

( i ) SEQUENCE CHARACTERISTICS:
        ( A ) LENGTH: 582 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 1..582

( x i ) SEQUENCE DESCRIPTION: SEQ ID NO:5:

```
ATG ACA AAC GAT AAT ATA AAG GAT TTG CTA GAC TGG TAT AGT AGT GGG        48
Met Thr Asn Asp Asn Ile Lys Asp Leu Leu Asp Trp Tyr Ser Ser Gly
 1               5                  10                  15

TCT GAC ACT TTT ACA AAT AGT GAA GTT TTA GAT AAT TCC TTA GGA TCT        96
Ser Asp Thr Phe Thr Asn Ser Glu Val Leu Asp Asn Ser Leu Gly Ser
             20                  25                  30

ATG CGT ATA AAA AAC ACA GAT GGC AGC ATC AGC CTT ATA ATT TTT CCG       144
Met Arg Ile Lys Asn Thr Asp Gly Ser Ile Ser Leu Ile Ile Phe Pro
         35                  40                  45

AGT CCT TAT TAT AGC CCT GCT TTT ACA AAA GGG GAA AAA GTT GAC TTA       192
Ser Pro Tyr Tyr Ser Pro Ala Phe Thr Lys Gly Glu Lys Val Asp Leu
     50                  55                  60

AAC ACA AAA AGA ACT AAA AAA AGC CAA CAT ACT AGC GAA GGA ACT TAT       240
Asn Thr Lys Arg Thr Lys Lys Ser Gln His Thr Ser Glu Gly Thr Tyr
 65                  70                  75                  80

ATC CAT TTC CAA ATA AGT GGC GTT ACA AAT ACT GAA AAA TTA CCT ACT       288
Ile His Phe Gln Ile Ser Gly Val Thr Asn Thr Glu Lys Leu Pro Thr
                 85                  90                  95

CCA ATA GAA CTA CCT TTA AAA GTT AAG GTT CAT GGT AAA GAT AGC CCC       336
Pro Ile Glu Leu Pro Leu Lys Val Lys Val His Gly Lys Asp Ser Pro
            100                 105                 110

TTA AAG TAT TGG CCA AAG TTC GAT AAA AAA CAA TTA GCT ATA TCA ACT       384
Leu Lys Tyr Trp Pro Lys Phe Asp Lys Lys Gln Leu Ala Ile Ser Thr
        115                 120                 125

TTA GAC TTT GAA ATT CGT CAT CAG CTA ACT CAA ATA CAT GGA TTA TAT       432
Leu Asp Phe Glu Ile Arg His Gln Leu Thr Gln Ile His Gly Leu Tyr
    130                 135                 140

CGT TCA AGC GAT AAA ACG GGT GGT TAT TGG AAA ATA ACA ATG AAT GAC       480
Arg Ser Ser Asp Lys Thr Gly Gly Tyr Trp Lys Ile Thr Met Asn Asp
145                 150                 155                 160

GGA TCC ACA TAT CAA AGT GAT TTA TCT AAA AAG TTT GAA TAC AAT ACT       528
Gly Ser Thr Tyr Gln Ser Asp Leu Ser Lys Lys Phe Glu Tyr Asn Thr
                165                 170                 175

GAA AAA CCA CCT ATA AAT ATT GAT GAA ATA AAA ACT ATA GAA GCA GAA       576
Glu Lys Pro Pro Ile Asn Ile Asp Glu Ile Lys Thr Ile Glu Ala Glu
            180                 185                 190

ATT AAT                                                               582
Ile Asn
```

( 2 ) INFORMATION FOR SEQ ID NO:6:

( i ) SEQUENCE CHARACTERISTICS:
        ( A ) LENGTH: 194 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Thr Asn Asp Asn Ile Lys Asp Leu Leu Asp Trp Tyr Ser Ser Gly

|   | 1 |   |   |   | 5 |   |   |   |   | 10 |   |   |   |   | 15 |   |
|---|---|---|---|---|---|---|---|---|---|---|---|---|---|---|---|---|
| Ser | Asp | Thr | Phe | Thr | Asn | Ser | Glu | Val | Leu | Asp | Asn | Ser | Leu | Gly | Ser |
|  |  |  | 20 |  |  |  | 25 |  |  |  |  | 30 |  |  |  |
| Met | Arg | Ile | Lys | Asn | Thr | Asp | Gly | Ser | Ile | Ser | Leu | Ile | Ile | Phe | Pro |
|  |  | 35 |  |  |  |  | 40 |  |  |  |  | 45 |  |  |  |
| Ser | Pro | Tyr | Tyr | Ser | Pro | Ala | Phe | Thr | Lys | Gly | Glu | Lys | Val | Asp | Leu |
|  | 50 |  |  |  |  | 55 |  |  |  |  | 60 |  |  |  |  |
| Asn | Thr | Lys | Arg | Thr | Lys | Lys | Ser | Gln | His | Thr | Ser | Glu | Gly | Thr | Tyr |
| 65 |  |  |  |  | 70 |  |  |  |  | 75 |  |  |  |  | 80 |
| Ile | His | Phe | Gln | Ile | Ser | Gly | Val | Thr | Asn | Thr | Glu | Lys | Leu | Pro | Thr |
|  |  |  |  | 85 |  |  |  |  | 90 |  |  |  |  | 95 |  |
| Pro | Ile | Glu | Leu | Pro | Leu | Lys | Val | Lys | Val | His | Gly | Lys | Asp | Ser | Pro |
|  |  |  | 100 |  |  |  |  | 105 |  |  |  |  | 110 |  |  |
| Leu | Lys | Tyr | Trp | Pro | Lys | Phe | Asp | Lys | Lys | Gln | Leu | Ala | Ile | Ser | Thr |
|  |  | 115 |  |  |  |  | 120 |  |  |  |  | 125 |  |  |  |
| Leu | Asp | Phe | Glu | Ile | Arg | His | Gln | Leu | Thr | Gln | Ile | His | Gly | Leu | Tyr |
|  | 130 |  |  |  |  | 135 |  |  |  |  | 140 |  |  |  |  |
| Arg | Ser | Ser | Asp | Lys | Thr | Gly | Gly | Tyr | Trp | Lys | Ile | Thr | Met | Asn | Asp |
| 145 |  |  |  |  | 150 |  |  |  |  | 155 |  |  |  |  | 160 |
| Gly | Ser | Thr | Tyr | Gln | Ser | Asp | Leu | Ser | Lys | Lys | Phe | Glu | Tyr | Asn | Thr |
|  |  |  |  | 165 |  |  |  |  | 170 |  |  |  |  | 175 |  |
| Glu | Lys | Pro | Pro | Ile | Asn | Ile | Asp | Glu | Ile | Lys | Thr | Ile | Glu | Ala | Glu |
|  |  |  | 180 |  |  |  |  | 185 |  |  |  |  | 190 |  |  |
| Ile | Asn |  |  |  |  |  |  |  |  |  |  |  |  |  |  |

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGGAATTCCA TGGAGAGTCA ACCAG         25

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GCGGATCCTC ACTTTTTCTT TGT         23

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GGGAATTCCA TGGAGAAAAG CG                                                                    22
```

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GCAAGCTTAA CTTGTATATA AATAG                                                                 25
```

( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CGGGGTACCC CGAAGGAGGA AAAAAAATG TCTACAAACG ATAATATAAA G                                      51
```

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
TGCTCTAGAG CATTAATTAA TTTCTGCTTC TATAGTTTTT AT                                               42
```

GENE THERAPY FOR T CELL REGULATION

This invention was made in part with government support AI00952-05, awarded by the National Institutes of Health. The government has certain rights to this invention.

FIELD OF THE INVENTION

The present invention relates to a product and process for regulating T cell activity by providing a superantigen gene, in the presence or absence of a cytokine gene. In particular, the present invention relates to a product and process for controlling tumor development, immune responses to infectious diseases and diseases caused by immunological disorders.

BACKGROUND OF THE INVENTION

Two major causes of disease include infectious agents and malfunctions of normal biological functions of an animal. Examples of infectious agents include viruses, bacteria, parasites, yeast and other fungi. Examples of abnormal biological function include uncontrolled cell growth, abnormal immune responses and abnormal inflammatory responses. Traditional reagents used attempt to protect an animal from disease include reagents that destroy infectious agents or cells involved in deregulated biological functions. Such reagents, however, can result in unwanted side effects. For example, anti-viral drugs that disrupt the replication of viral DNA also often disrupt DNA replication in normal cells in the treated patient. Other treatments with chemotherapeutic reagents to destroy cancer cells typically leads to side effects, such as bleeding, vomiting, diarrhea, ulcers, hair loss and increased susceptibility to secondary cancers and infections.

An alternative method of disease treatment includes modulating the immune system of a patient to assist the patient's natural defense mechanisms. Traditional reagents and methods used to attempt to regulate an immune response in a patient also result in unwanted side effects and have limited effectiveness. For example, immunosuppressive reagents (e.g., cyclosporin A, azathioprine, and prednisone) used to treat patients with autoimmune disease also suppress the patient's entire immune response, thereby increasing the risk of infection. In addition, immunopharmacological reagents used to treat cancer (e.g., interleukins) are short-lived in the circulation of a patient and are ineffective except in large doses. Due to the medical importance of immune regulation and the inadequacies of existing immunopharmacological reagents, reagents and methods to regulate specific parts of the immune system have been the subject of study for many years.

Stimulation or suppression of the immune response in a patient can be an effective treatment for a wide variety of medical disorders. T lymphocytes (T cells) are one of a variety of distinct cell types involved in an immune response. The activity of T cells is regulated by antigen, presented to a T cell in the context of a major histocompatibility complex (MHC) molecule. The T cell receptor (TCR) then binds to the MHC:antigen complex. Once antigen is complexed to MHC, the MHC:antigen complex is bound by a specific TCR on a T cell, thereby altering the activity of that T cell.

The use of certain staphylococcal enterotoxin proteins that are capable of complexing with MHC molecules to influence T cell function has been suggested by various investigators, including, for example, White et al., *Cell* 56:27–35, 1989; Rellahan et al. *J. Expt. Med.* 172:1091–1100, 1990; Micusan et al., *Immunology* 5:3–11, 1993; Hermann et al., *Immunology* 5:33–39, 1993; Bhardwaj et al., *J. Expt. Med.* 178:633–642, 1993; and Kalland et al., *Med. Oncol. & Tumor Pharmacother,* 10:37–47, 1993. In particular, various investigators have suggested that *Staphylococcal enterotoxin* proteins are useful for treating tumors, including Newell et al., *Proc. Natl. Acad. Sci. USA* 88:1074–1078, 1991; Kalland et al., PCT Application No. WO 91/04053, published Apr. 4, 1991; Dohlstein et al., *Proc. Natl. Acad. Sci. USA* 88:9287–9291, 1991; Hedlund et al., *Cancer Immunol. Immunother.* 36:89–93, 1993; Lando et al., *Cancer Immunol. Immunother.* 36:223–228, 1993; Lukacs et al., *J. Exp. Med.* 178:343–348, 1993; Ochi et al., *J. Immunol.* 151:3180–3186, 1993; and Terman et al., PCT Application No. WO 93/24136, published Dec. 9, 1993. These investigators, however, have only disclosed the use of bacterial enterotoxin proteins themselves. The use of bacterial enterotoxin protein has the major disadvantage of being toxic to the recipient of the protein.

Thus, there is a need for a product and process that allows for the treatment of disease using bacterial enterotoxins in a non-toxic manner.

SUMMARY

Traditional pharmaceutical reagents used to treat cancer, infectious diseases and diseases caused by immunological disorders often have harmful side effects. In addition, such reagents can be unpredictable (e.g., chemotherapy treatment of cancer). The present invention provides a therapeutic composition having at least two components: (a) an isolated nucleic acid molecule encoding a superantigen; and (b) an isolated nucleic acid molecule encoding a cytokine; as well as methods to use the composition to control cellular immunity and thereby treat a variety of diseases.

The invention is particularly advantageous in that it provides an effective therapeutic composition that enables the safe treatment of an animal with a potentially toxic and immunogenic protein. Upon delivery, expression of the nucleic acid molecules contained in the therapeutic composition result in localized production of an effective but non-toxic amount of an encoded protein that is toxic at concentrations required when the encoded protein is itself administered. The therapeutic compositions of the present invention can provide long term expression of the encoded proteins at a site in an animal. Such long term expression allows for the maintenance of an effective, but non-toxic, dose of the encoded protein to treat a disease and limits the frequency of administration of the therapeutic composition needed to treat an animal. In addition, because of the lack of toxicity, therapeutic compositions of the present invention can be used in repeated treatments.

One embodiment of the present invention is a therapeutic composition comprising an isolated nucleic acid molecule encoding a superantigen and an isolated nucleic acid molecule encoding a cytokine, in which the isolated nucleic acid molecules are operatively linked to one or more transcription control sequences. Preferred superantigen-encoding nucleic acid molecules encode, for example, staphylococcal enterotoxins, retroviral antigens, streptococcal antigens, mycoplasma antigens, mycobacteria antigens, viral antigens and/or protozoan antigens. Preferred cytokine-encoding nucleic acid molecules encode, for example, hematopoietic growth factors, interleukins, interferons, immunoglobulin superfamily molecules, tumor necrosis factor family molecules and chemokines. Preferably, a nucleic acid molecule of the present invention is complexed with a delivery vehicle, such as a liposome.

Another embodiment of the present invention includes a recombinant molecule comprising an isolated nucleic acid molecule encoding a superantigen and an isolated nucleic acid molecule encoding a cytokine, in which the isolated nucleic acid molecules are operatively linked to one or more transcription control sequences. Preferably, such transcription control sequences comprise, for example, RSV control sequences, CMV control sequences, retroviral LTR control sequences, SV-40 control sequences and β-actin control sequences.

Another aspect of the present invention includes a method to treat an animal that has cancer. The method includes the steps of administering to the animal an effective amount of a therapeutic composition comprising (a) an isolated nucleic acid molecule encoding a superantigen and (b) an isolated nucleic acid molecule encoding a cytokine, in which the nucleic acid molecules are operatively linked to one or more transcription control sequences, and in which the therapeutic composition is targeted to the site of a cancer in the animal to treat the cancer. The method is useful for the treatment of many different types of cancer. Preferred cancers to treat include melanomas, lung cancers, thyroid carcinomas, breast cancers, renal cell carcinomas, squamous cell carcinomas, brain tumors and/or skin cancers.

The present invention also includes a method for increasing effector cell activity in an animal. The method includes the steps of administering to an animal an effective amount of a therapeutic composition comprising a) an isolated nucleic acid molecule encoding a superantigen and b) an isolated nucleic acid molecule encoding a cytokine, in which the isolated nucleic acid molecules are operatively linked to one or more transcription control sequences, and in which the therapeutic composition is targeted to a site in the animal that contains an abnormal cell. Preferably, the abnormal cell, includes a cancer cell, a cell infected with an infectious agent or a non-cancerous cell having abnormal proliferative growth.

Another aspect of the present includes a method to suppress T cell activity in an animal, the method comprising administering to an animal an effective amount of a therapeutic composition comprising a naked isolated nucleic acid molecule encoding a superantigen and a pharmaceutically acceptable carrier, in which the isolated nucleic acid molecule is operatively linked to a transcription control sequence, and in which the therapeutic composition is targeted to a site in the animal that contains excessive T cell activity. Preferably, the composition is capable of suppressing the T cell activity for at least about 6 weeks, more preferably for at least about 8 weeks and even more preferably for at least about 10 weeks in the animal.

DETAILED DESCRIPTION OF THE INVENTION

Figure 1:
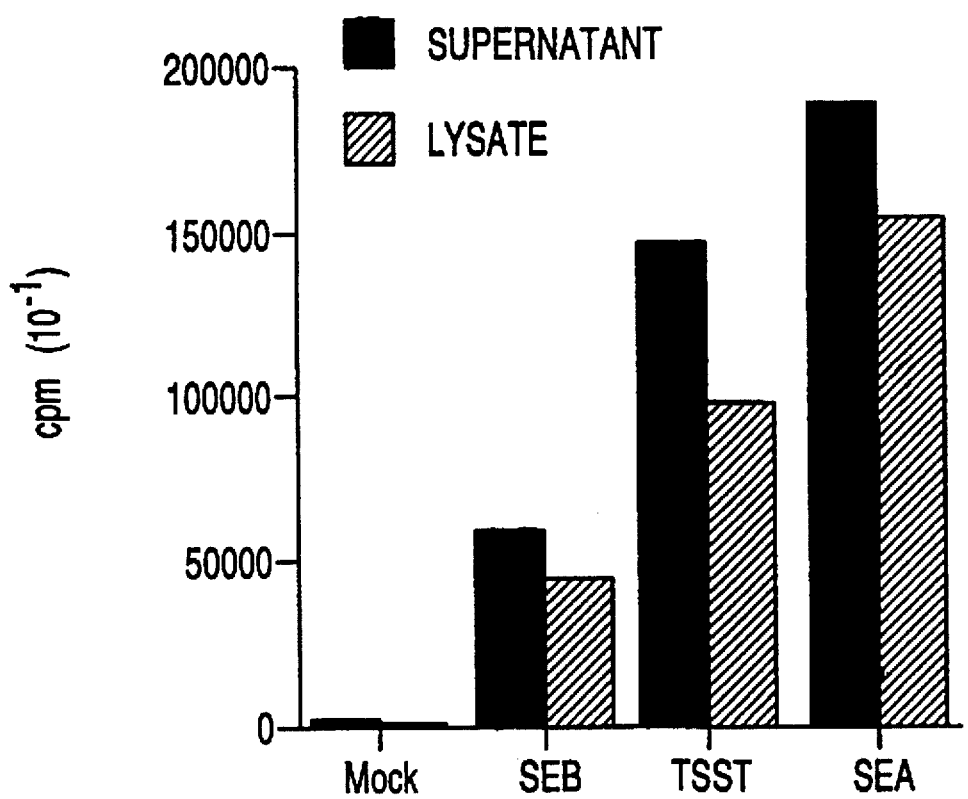
FIG. 1 illustrates the expression of superantigen-encoding DNA plasmids in mammalian cells.

The present invention relates to a novel product and process for controlling effector cell activity. It is now known for the first time that a composition containing nucleic acid molecules encoding a superantigen, rather than superantigen proteins, is an effective therapeutic reagent for treating disease. The present inventors have also discovered that administration of a combination of nucleic acid molecules encoding a superantigen and a cytokine can act synergistically to effectively treat cancer and infectious disease. The present invention includes a therapeutic composition having at least two components: (a) an isolated nucleic acid molecule encoding a superantigen; and (b) an isolated nucleic acid molecule encoding a cytokine. Administration of a therapeutic composition of the present invention to an animal results in the production of superantigen and cytokine proteins, referred to herein as "encoded proteins." Each of the components of a therapeutic composition of the present invention is described in detail below, followed by a description of the methods by which the therapeutic composition is used and delivered.

One embodiment of the present invention includes a method for increasing effector cell immunity in an animal, the method comprising administering to an animal an effective amount of a therapeutic composition comprising: (a) an isolated nucleic acid molecule encoding a superantigen; and (b) an isolated nucleic acid molecule encoding a cytokine, in which the nucleic acid molecules are operatively linked to one or more transcription control sequences, and in which the therapeutic composition is targeted to a site in the animal that contains an abnormal cell. According to the present invention, an effector cell, includes a helper T cell, a cytotoxic T cell, a macrophage, a monocyte and/or a natural killer cell. For example, the method of the present invention can be performed to increase the number of effector cells in an animal that are capable of killing or releasing cytokines when presented with antigens derived from an abnormal cell or a pathogen. An effective amount of a therapeutic composition of the present invention comprises an amount capable of treating a disease as described herein. Alternatively, a method of the present invention can be performed to decrease the number of T cells found in a T cell subset that is preferentially stimulated and expanded by an autoantigen.

As used herein, effector cell immunity refers to increasing the number and/or the activity of effector cells in the area of the abnormal cell. In particular, T cell activity refers to increasing the number and/or the activity of T cells in the area of the abnormal cell. Also, as used herein, an abnormal cell refers to a cell displaying abnormal biological function, such as abnormal growth, development or death. Abnormal cells of the present invention, preferably includes cancer cells, cells infected with an infectious agent (i.e., a pathogen) and non-cancerous cells having abnormal proliferative growth (e.g., sarcoidosis, granulomatous disease or papillomas) and with cancer cells and infected cells.

Another embodiment of the present invention is a method to treat an animal with cancer, the method comprising administering to an animal an effective amount of a therapeutic composition comprising: (a) a nucleic acid molecule encoding a superantigen; and (b) a nucleic acid molecule encoding a cytokine, in which the nucleic acid molecules are operatively linked to one or more transcription control sequences, and in which the therapeutic composition is targeted to the site of a cancer.

One embodiment of a therapeutic composition of the present invention comprises an isolated nucleic acid molecule encoding a superantigen (also referred to herein as a "superantigen-encoding" nucleic acid molecule) and an isolated nucleic acid molecule encoding a cytokine (also referred to herein as a "cytokine-encoding" nucleic acid molecule), in which the nucleic acid molecules are operatively linked to one or more transcription control sequences. It is to be noted that the term "a" or "an" entity refers to one or more of that entity; for example, a compound refers to one or more compounds. As such, the terms "a" (or "an"), "one or more" and "at least one" can be used interchangeably herein. According to the present invention, an isolated, or biologically pure, nucleic acid molecule, is a nucleic acid molecule that has been removed from its natural milieu. As such, "isolated" and "biologically pure" do not necessarily reflect the extent to which the nucleic acid molecule has been purified. An isolated nucleic acid molecule can include DNA, RNA, or derivatives of either DNA or RNA. An isolated superantigen or cytokine nucleic acid molecule can be obtained from its natural source, either as an entire (i.e., complete) gene or a portion thereof capable of encoding a superantigen protein capable of binding to an MHC molecule or a cytokine protein capable of binding to a complementary cytokine receptor. A nucleic acid molecule can also be produced using recombinant DNA technology (e.g., polymerase chain reaction (PCR) amplification, cloning) or chemical synthesis. Nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a functional superantigen or a functional cytokine of the present invention.

A nucleic acid molecule homologue can be produced using a number of methods known to those skilled in the art (see, for example, Sambrook et al., *Molecular Cloning: A Laboratory Manual*, Cold Spring Harbor Labs Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., superantigen or cytokine activity, as appropriate). Techniques to screen for superantigen or cytokine activity are known to those of skill in the art.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a superantigen or a cytokine protein. In addition, the phrase "recombinant molecule" primarily refers to a nucleic acid molecule operatively linked to a transcription control sequence, but can be used interchangeably with the phrase "nucleic acid molecule" which is administered to an animal. As heretofore disclosed, superantigen or cytokine proteins of the present invention include, but are not limited to, proteins having full-length superantigen or cytokine coding regions, proteins having partial superantigen regions capable of binding to an MHC molecule, cytokine coding regions capable of binding to a complementary cytokine receptor, fusion proteins and chimeric proteins comprising combinations of different superantigens and/or cytokines.

One embodiment of the present invention is an isolated superantigen-encoding nucleic acid molecule that encodes at least a portion of a full-length superantigen, or a homologue of a superantigen. As used herein, "at least a portion of a superantigen" refers to a portion of a superantigen protein capable of binding to an MHC molecule in such a manner that a TCR can bind to the resulting superantigen:MHC complex. Preferably, a superantigen nucleic acid molecule of the present invention encodes an entire coding region of a superantigen, and more preferably the coding region absent a leader sequence. Production of a truncated superantigen protein lacking a bacterial leader sequence is preferred to enhance secretion of the superantigen from a cell. As used herein, a homologue of a superantigen is a protein having an amino acid sequence that is sufficiently similar to a natural superantigen amino acid sequence that a nucleic acid sequence encoding the homologue encodes a protein capable of binding to an MHC molecule.

In accordance with the present invention, a superantigen comprises a family of T cell regulatory proteins that are capable of binding both to an MHC molecule. A superantigen binds to the extracellular portion of an MHC molecule to form and MHC:superantigen complex. The activity of a T cell can be modified when a TCR binds to an MHC:superantigen complex. Under certain circumstances, an MHC:superantigen complex can have a mitogenic role (i.e., the ability to stimulate the proliferation of T cells) or a suppressive role (i.e., deletion of T cell subsets). The ability of an MHC:superantigen complex to have a stimulatory or suppressive role can depend upon factors, such as the concentration and environment (i.e., tissue location and/or the presence of cytokines).

The mitogenic role of a superantigen is distinct from other known mitogens (e.g., lectins derived from plants) in that superantigens are capable of stimulating the proliferation of particular subsets of T cells having TCR's that specifically bind to the superantigen. For example, a superantigen, when added to a mixed lymphocyte population, is able to stimulate the proliferation of a select population of T cells from the mixed population of cells. Examples of T cell subsets stimulated by superantigens complexed with MHC molecules include T cells expressing a TCR comprising mouse $V_\beta 1$, $V_\beta 3$, $V_\beta 7$, $V_\beta 8.1$, $V_\beta 8.2$, $V_\beta 8.3$, $V_\beta 10$, $V_\beta 11$, $V_\beta 17$, $V_\beta 15$ or $V_\beta 16$ chains, and T cells expressing a TCR comprising human $V_\beta 1.1$, $V_\beta 2$, $V_\beta 3$, $V_\beta 5$, $V_\beta 6$, $V_\beta 7.3$, $V_\beta 7.4$, $V_\beta 9.1$, $V_\beta 12$, $V_\beta 14$, $V_\beta 15$, $V_\beta 17$ or $V_\beta 20$ chains.

A superantigen-encoding nucleic acid molecule of the present invention preferably encodes superantigens that includes, but is not limited to, staphylococcal enterotoxins, retroviral antigens, streptococcal antigens, mycoplasma antigens, mycobacterium antigens, viral antigens (e.g., a superantigen from mouse mammary tumor virus, rabies virus or herpes virus) and endoparasitic antigens (e.g., protozoan or helminth antigens), more preferably *staphylococcal enterotoxins*, and even more preferably *Staphylococcal enterotoxin* A (SEA), *Staphylococcal enterotoxin* B (SEB), *Staphylococcal enterotoxin* $C_1$ ($SEC_1$), *Staphylococcal enterotoxin* $C_2$ ($SEC_2$), *Staphylococcal enterotoxin* $C_3$ ($SEC_3$), *Staphylococcal enterotoxin* D (SED), *Staphylococcal enterotoxin* E (SEE) and Toxic Shock Syndrome Toxin (TSST).

A preferred nucleic acid molecule encoding a *Staphylococcal enterotoxin* of the present invention comprises a nucleic acid sequence represented by SEQ ID NO:1 (representing a full-length SEB gene), SEQ ID NO:3 (representing a full-length SEA gene) or SEQ ID NO:6 (representing a full-length TSST gene). A preferred *Staphylococcal enterotoxin* protein of the present invention comprises an amino acid sequence represented by SEQ ID NO:2 (representing a full-length SEB protein), SEQ ID NO:4 (representing a full-length SEA protein) or SEQ ID NO:7 (representing a full-length TSST protein).

In a preferred embodiment, a nucleic acid molecule of the present invention encoding a superantigen comprises a nucleic acid sequence spanning base pair 46 to at least base pair 768 of SEQ ID NO:1, a nucleic acid sequence spanning base pair 46 to about base pair 751 of SEQ ID NO:3 or SEQ ID NO:6.

Another embodiment of the present invention includes a cytokine-encoding nucleic acid molecule that encodes a full-length cytokine or a homologue of the cytokine protein. As used herein, a homologue of a cytokine is a protein having an amino acid sequence that is sufficiently similar to a natural cytokine amino acid sequence so as to have cytokine activity. In accordance with the present invention, a cytokine includes a protein that is capable of affecting the biological function of another cell. A biological function affected by a cytokine can include, but is not limited to, cell growth, cell differentiation or cell death. Preferably, a cytokine of the present invention is capable of binding to a specific receptor on the surface of a cell, thereby affecting the biological function of a cell.

A cytokine-encoding nucleic acid molecule of the present invention encodes a cytokine that is capable of affecting the biological function of a cell, including, but not limited to, a lymphocyte, a muscle cell, a hematopoietic precursor cell, a mast cell, a natural killer cell, a macrophage, a monocyte, an epithelial cell, an endothelial cell, a dendritic cell, a mesenchymal cell, a Langerhans cell, cells found in granulomas and tumor cells of any cellular origin, and more preferably a mesenchymal cell, an epithelial cell, an endothelial cell, a muscle cell, a macrophage, a monocyte, a T cell and a dendritic cell.

A preferred cytokine nucleic acid molecule of the present invention encodes a hematopoietic growth factor, an interleukin, an interferon, an immunoglobulin superfamily molecule, a tumor necrosis factor family molecule and/or a chemokine (i.e., a protein that regulates the migration and activation of cells, particularly phagocytic cells). A more preferred cytokine nucleic acid molecule of the present invention encodes a granulocyte macrophage colony stimulating factor (GM-CSF), tumor necrosis factor α (TNF-α), macrophage colony stimulating factor (M-CSF), interleukin-1 (IL-1), interleukin-6 (IL-6) and/or interleukin-12 (IL-12). An even more preferred cytokine nucleic acid molecule of the present invention encodes GM-CSF and/or TNF-α, with GM-CSF being even more preferred.

As will be apparent to one of skill in the art, the present invention is intended to apply to cytokines derived from all types of animals. A preferred animal from which to derive cytokines includes a mouse, a human and a dog. A more preferred animal from which to derive cytokines includes a dog and a human. An even more preferred animal from which to derive cytokines is a human.

According to the present invention, a cytokine-encoding nucleic acid molecule of the present invention is derived from the same species of animal as the animal to be treated. For example, a cytokine-encoding nucleic acid molecule derived from a canine (i.e., dog) nucleic acid molecule is used to treat a disease in a canine. Thus, a preferred cytokine-encoding nucleic acid molecule of the present invention comprises a nucleic acid molecule encoding human GM-CSF, as described in the art. A human GM-CSF-encoding nucleic acid molecule of the present invention can be produced using methods standard PCR amplification methods with primers designed from the human GM-CSF nucleic acid sequence disclosed in Nash (*Blood* 78:930, 1991). Such PCR products can be cloned into a $PCR_3$ expression vector using the methods generally described in Example 1.

The present invention includes a nucleic acid molecule of the present invention operatively linked to one or more transcription control sequences to form a recombinant molecule. The phrase "operatively linked" refers to linking a nucleic acid molecule to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, insect cells, and preferably in animal cells. More preferred transcription control sequences include, but are not limited to, simian virus 40 (SV-40), β-actin, retroviral long terminal repeat (LTR), Rous sarcoma virus (RSV), cytomegalovirus (CMV), tac, lac, trp, trc, oxy-pro, omp/lpp, rrnB, bacteriophage lambda (λ) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus and other poxviruses, herpesvirus, and adenovirus transcription control sequences, as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding a superantigen or a cytokine of the present invention.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention also contains secretory signals (i.e., signal segment nucleic acid sequences) to enable an expressed superantigen or cytokine protein to be secreted from the cell that produces the protein. Suitable signal segments include: (1) a bacterial signal segment, in particular a superantigen signal segment; (2) a cytokine signal segment; (3) or any heterologous signal segment capable of directing the secretion of a superantigen and/or cytokine protein of the present invention. Preferred signal segments include, but are not limited to, signal segments associated with SEB, SEA, TSST, GM-CSF, M-CSF, TNFα, IL-1, IL-6 and IL-12 protein.

Preferred recombinant molecules of the present invention include a recombinant molecule containing a nucleic acid molecule encoding a superantigen, a recombinant molecule containing a nucleic acid molecule encoding a cytokine, or a recombinant molecule containing a nucleic acid molecule encoding a superantigen and a nucleic acid molecule encoding a cytokine to form a chimeric recombinant molecule. The nucleic acid molecules contained in such a recombinant chimeric molecule are operatively linked to one or more transcription control sequences, in which each nucleic acid molecule contained in a chimeric recombinant molecule can be expressed using the same or different regulatory control sequences. Preferred recombinant molecules of the present invention comprise a nucleic acid sequence represented by SEQ ID NO:1, SEQ ID NO:3, SEQ ID NO:5, or combinations thereof. Particularly preferred recombinant molecules include $PCR_3$-SEB, $PCR_3$-SEA, $PCR_3$-SEB.S, $PCR_3$-SEA.S, $PCR_3$-TSST and $PCR_3$-$GM_3$, the production of which is disclosed herein.

One or more recombinant molecules of the present invention can be used to produce an encoded product (i.e., a superantigen protein and a cytokine protein) of the present invention. In one embodiment, an encoded product of the present invention is produced by expressing a nucleic acid molecule of the present invention under conditions effective to produce the protein. A preferred method to produce an encoded protein is by transfecting a host cell with one or more recombinant molecules of the present invention to form a recombinant cell. Suitable host cells to transfect include any cell that can be transfected. Host cells can be either untransfected cells or cells that are already transformed with at least one nucleic acid molecule. Host cells of the present invention can be any cell capable of producing a superantigen and/or a cytokine of the present invention, including bacterial, fungal, animal parasite, insect and animal cells. A preferred host cell includes a mammalian and a bird cell. A more preferred host cell includes mammalian lymphocytes, muscle cells, hematopoietic precursor cells, mast cells, natural killer cells, macrophages, monocytes, epithelial cells, endothelial cells, dendritic cells, mesenchymal cells, Langerhans cells, cells found in granulomas and tumor cells of any cellular origin. An even more preferred host cell of the present invention includes mammalian mesenchymal cells, epithelial cells, endothelial cells, macrophages, monocytes, muscle cells, T cells and dendritic cells.

According to the present invention, a host cell can be transfected in vivo (i.e., in an animal) or in vitro (i.e., outside of an animal, such as in tissue culture). Transfection of a nucleic acid molecule into a host cell can be accomplished by any method by which a nucleic acid molecule can be inserted into the cell. Transfection techniques include, but are not limited to, transfection, electroporation, microinjection, lipofection, adsorption, and protoplast fusion. Preferred methods to transfect host cells in vivo include lipofection and adsorption (discussed in detail below).

A recombinant cell of the present invention comprises a cell transfected with a nucleic acid molecule that encodes a superantigen and/or a cytokine. Preferably, if T cell stimulation is desired, a cell is transfected with a nucleic acid molecule encoding a superantigen and a cytokine. If T cell suppression is desired, a cell is transfected with only a nucleic acid molecule encoding a superantigen.

In a preferred embodiment, a recombinant cell useful for stimulating a T cell response is a cell transfected with a recombinant molecule $PCR_3$-SEB, $PCR_3$-SEA, $PCR_3$-SEB.S, $PCR_3$-SEA.S, $PCR_3$-TSST or combinations thereof, and $PCR_3$-$GM_3$. Particularly preferred stimulatory recombinant cells include cells transfected with $PCR_3$-SEA and $PCR_3$-$GM_3$, $PCR_3$-SEA.S and $PCR_3$-$GM_3$, $PCR_3$-SEB and $PCR_3$-$GM_3$, $PCR_3$-SEB.S and $PCR_3$-$GM_3$, or $PCR_3$-TSST and $PCR_3$-$GM_3$. Even more preferred stimulatory recombinant cells include cells transfected with $PCR_3$-SEB.S and $PCR_3$-$GM_3$, or $PCR_3$-SEA.S and $PCR_3$-$GM_3$, and $PCR_3$-TSST and $PCR_3$-$GM_3$.

In another preferred embodiment, a recombinant cell useful for suppressing a T cell response is a cell transfected with a nucleic acid molecule that includes at least a portion of $PCR_3$-SEB, $PCR_3$-SEA, $PCR_3$-SEB.S, $PCR_3$-SEA.S, $PCR_3$-TSST, or combinations thereof. Particularly preferred recombinant cells include cells transfected with $PCR_3$-SEB, $PCR_3$-SEA, $PCR_3$-SEB.S, $PCR_3$-SEA.S or $PCR_3$-TSST, with $PCR_3$-SEB.S, $PCR_3$-SEA.S or $PCR_3$-TSST being even more preferred.

It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein.

In another embodiment of the present invention, a therapeutic composition further comprises a pharmaceutically acceptable carrier. As used herein, a "carrier" refers to any substance suitable as a vehicle for delivering a nucleic acid molecule of the present invention to a suitable in vivo or in vitro site. As such, carriers can act as a pharmaceutically acceptable excipient of a therapeutic composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in an animal or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to an animal, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods and/or lyophilizedo Targeting carriers are herein referred to as "delivery vehicles." Delivery vehicles of the present invention are capable of delivering a therapeutic composition of the present invention to a target site in an animal. A "target site" refers to a site in an animal to which one desires to deliver a therapeutic composition. For example, a target site can be a cancer cell, a tumor, or a lesion caused by an infectious agent, or an area around such cell, tumor or leasion, which is targeted by direct injection or delivery using liposomes or other delivery vehicles. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelies. A delivery vehicle of the present invention can be modified to target to a particular site in an animal, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a cancer cell can be introduced to the outer surface of a liposome delivery vehicle so as to target the delivery vehicle to the cancer cell. Tumor cell ligands include ligands capable of binding to a molecule on the surface of a tumor cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

A preferred delivery vehicle of the present invention is a liposome. A liposome is capable of remaining stable in an animal for a sufficient amount of time to deliver a nucleic acid molecule of the present invention to a preferred site in the animal. A liposome of the present invention is preferably stable in the animal into which it has been administered for at least about 30 minutes, more preferably for at least about 1 hour and even more preferably for at least about 24 hours.

A liposome of the present invention comprises a lipid composition that is capable of targeting a nucleic acid molecule of the present invention to a particular, or selected, site in an animal. Preferably, the lipid composition of the liposome is capable of targeting to any organ of an animal, more preferably to the lung, liver, spleen, heart brain, lymph nodes and skin of an animal, and even more preferably to the lung of an animal.

A liposome of the present invention comprises a lipid composition that is capable of fusing with the plasma membrane of the targeted cell to deliver a nucleic acid molecule into a cell. Preferably, the transfection efficiency of a liposome of the present invention is about 0.5 microgram (µg) of DNA per 16 nanomole (nmol) of liposome delivered to about $10^6$ cells, more preferably about 1.0 µg of DNA per 16 nmol of liposome delivered to about $10^6$ cells, and even more preferably about 2.0 µg of DNA per 16 nmol of liposome delivered to about $10^6$ cells.

A preferred liposome of the present invention is between about 100 and 500 nanometers (nm), more preferably between about 150 and 450 nm and even more preferably between about 200 and 400 nm in diameter.

Suitable liposomes for use with the present invention include any liposome. Preferred liposomes of the present invention include those liposomes standardly used in, for example, gene delivery methods known to those of skill in the art. More preferred liposomes comprise liposomes having a polycationic lipid composition and/or liposomes having a cholesterol backbone conjugated to polyethylene glycol. Even more preferred liposomes include liposomes produced according to the method described in Example 2.

In one embodiment, a liposome of the present invention comprises a compound capable of targeting the liposome to a tumor cell. Such a liposome preferably includes a tumor cell ligand exposed on the outer surface of the liposome.

Complexing a liposome with a nucleic acid molecule of the present invention can be achieved using methods standard in the art (see, for example, methods described in Example 2). A suitable concentration of a nucleic acid molecule of the present invention to add to a liposome includes a concentration effective for delivering a sufficient amount of nucleic acid molecule to a cell such that the cell can produce sufficient superantigen and/or cytokine protein to regulate effector cell immunity in a desired manner. Preferably, from about 0.1 µg to about 10 µg of nucleic acid molecule of the present invention is combined with about 8 nmol liposomes, more preferably from about 0.5 µg to about 5 µg of nucleic acid molecule is combined with about 8 nmol liposomes, and even more preferably about 1.0 µg of nucleic acid molecule is combined with about 8 nmol liposomes.

Another preferred delivery vehicle comprises a recombinant virus particle vaccine. A recombinant virus particle vaccine of the present invention includes a therapeutic composition of the present invention, in which the recombinant molecules contained in the composition are packaged in a viral coat that allows entrance of DNA into a cell so that the DNA is expressed in the cell. A number of recombinant virus particles can be used, including, but not limited to, those based on alphaviruses, poxviruses, adenoviruses, herpesviruses, arena virus and retroviruses.

Another preferred delivery vehicle comprises a recombinant cell vaccine. Preferred recombinant cell vaccines of the present invention include tumor vaccines, in which allogeneic (i.e., cells derived from a source other than a patient, but that are histiotype compatible with the patient) or autologous (i.e., cells isolated from a patient) tumor cells are transfected with recombinant molecules contained in a therapeutic composition, irradiated and administered to a patient by, for example, intradermal, intravenous or subcutaneous injection. Therapeutic compositions to be administered by tumor cell vaccine, include recombinant molecules of the present invention without carrier. Tumor cell vaccine treatment is useful for the treatment of both tumor and metastatic cancer. Use of a tumor vaccine of the present invention is particular useful for treating metastatic cancer, including preventing metastatic disease, as well as, curing existing metastatic disease. Methods for developing and administering include those standard in the art (see for example, Dranoff et al., Proc. Natl. Acad. Sci. USA 90:3539–3543, 1993, which is incorporated herein by reference in its entirety).

A therapeutic composition of the present invention is useful for the treatment of a variety of diseases, including, but not limited to, cancer, autoimmune disease, infectious diseases, and other diseases that can be alleviated by either stimulating or suppressing T cell activity. A therapeutic composition of the present invention is advantageous for the treatment of cancer in that the composition overcomes the mechanisms by which cancer cells avoid immune elimination (i.e., by which cancer cells avoid the immune response effected by the animal in response to the disease). Cancer cells can avoid immune elimination by, for example, being only slightly immunogenic, modulating cell surface antigens and inducing immune suppression. A suitable therapeutic composition for use in the treatment of cancer comprises a combination of a superantigen-encoding recombinant molecule and a cytokine-encoding recombinant molecule of the present invention. A more preferred therapeutic composition for use in the treatment of cancer comprises a combination of a superantigen-encoding recombinant molecule and a cytokine-encoding recombinant molecule of the present invention combined (separately or together) with a delivery vehicle, preferably a liposome, such as disclosed herein. A therapeutic composition of the present invention, upon entering targeted cells, leads to the production of superantigen and cytokine protein that activate cytotoxic T cells, natural killer cells, T helper cells and macrophages. Such cellular activation overcomes the otherwise relative lack of immune response to cancer cells, leading to the destruction of such cells.

A therapeutic composition of the present invention is useful for the treatment of cancers, both tumors and metastatic forms of cancer. Treatment with the therapeutic composition overcomes the disadvantages of traditional treatments for metastatic cancers. For example, compositions of the present invention can target dispersed metastatic cancer cells that cannot be treated using surgical methods. In addition, administration of such compositions do not result in the harmful side effects caused by chemotherapy and radiation therapy.

A therapeutic composition of the present invention is preferably used to treat cancers, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, leukemias and lymphomas. Particularly preferred cancers to treat with a therapeutic composition of the present invention, include melanomas, lung cancers, thyroid carcinomas, breast cancers, renal cell carcinomas, squamous cell carcinomas, brain tumors and skin cancers. A therapeutic composition of the present invention is useful for treating tumors that can form in such cancers, including malignant and benign tumors.

A therapeutic composition of the present invention is also advantageous for the treatment of infectious diseases as a long term, targeted therapy for primary lesions (e.g., granulomas) resulting from the propagation of a pathogen. As used herein, the term "lesion" refers to a lesion formed by infection of an animal with a pathogen. A preferred therapeutic composition for use in the treatment of an infectious disease comprises a superantigen-encoding recombinant molecule and a cytokine-encoding recombinant molecule of the present invention. A more preferred therapeutic composition for use in the treatment of infectious disease comprises a superantigen-encoding recombinant molecule and a cytokine-encoding recombinant molecule of the present invention combined with a delivery vehicle, preferably a liposome of the present invention. Similar to the mechanism described for the treatment of cancer, treatment of infectious diseases with superantigen and cytokine can result in increased T cell, natural killer cell, and macrophage cell activity that overcome the relative lack of immune response to a lesion formed by a pathogen. A therapeutic composition of the present invention is particularly useful for the treatment of infectious diseases caused by pathogens, including, but not limited to, intracellular bacteria (i.e., a bacteria that resides in a host cell), internal parasites, pathogenic fungi and endoparasites. Particularly preferred infectious diseases to treat with a therapeutic composition of the present invention include tuberculosis, leprosy, aspergillosis, coccidioidomycosis, cryptococcoses, leishmaniasis and toxoplasmosis.

In order to treat an animal with disease, a therapeutic composition of the present invention is administered to the animal in an effective manner such that the composition is capable of treating that animal from disease. For example, a recombinant molecule, when administered to an animal in an effective manner, is able to stimulate effector cell immunity in a manner that is sufficient to alleviate the disease afflicting the animal. According to the present invention, treatment of a disease refers to alleviating a disease and/or preventing the development of a secondary disease resulting from the occurrence of a primary disease. An effective administration protocol (i.e., administering a therapeutic composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease. In particular, the effectiveness of dose parameters and modes of administration of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of treating an animal with disease when administered one or more times over a suitable time period. Doses can vary depending upon the disease being treated. In the treatment of cancer, a suitable single dose can be dependent upon whether the cancer being treated is a primary tumor or a metastatic form of cancer. Doses of a therapeutic composition of the present invention suitable for use with direct injection techniques can be used by one of skill in the art to determine appropriate single dose sizes for systemic administration based on the size of an animal. A suitable single dose of a therapeutic composition to treat a tumor is a sufficient amount of a superantigen-encoding recombinant molecule and a cytokine-encoding recombinant molecule to reduce, and preferably eliminate, the tumor following transfection of the recombinant molecules into cells at or near the tumor site. A preferred single dose of the superantigen-encoding recombinant molecule is an amount that, when transfected into a target cell population leads to the production of from about 250 femtograms (fg) to about 1 µg, preferably from about 500 fg to about 500 picogram (pg), and more preferably from about 1 pg to about 100 pg of superantigen per transfected cell. A preferred single dose of a cytokine-encoding recombinant molecule is an amount that when transfected into a target cell population leads to the production of from about 10 pg to about 1 µg, preferably from about 100 pg to about 750 pg, and more preferably about 500 pg of cytokine per transfected.

A suitable single dose of a superantigen-encoding recombinant molecule and a cytokine-encoding recombinant molecule in a non-targeting carrier to administer to an animal to treat a tumor, is an amount capable of reducing, and preferably eliminating, the tumor following transfection of the recombinant molecules into cells at or near the tumor site. A preferred single dose of a therapeutic composition to treat a tumor is from about 100 µg to about 2 milligrams (mg) of total recombinant molecules, more preferably from about 150 µg to about 1 mg of total recombinant molecules, and even more preferably from about 200 µg to about 800 µg of total recombinant molecules. A preferred single dose of a superantigen-encoding recombinant molecule complexed with liposomes, is from about 100 µg of total DNA per 800 nmol of liposome to about 2 mg of total recombinant molecules per 16 micromole (µmol) of liposome, more preferably from about 150 µg per 1.2 µmol of liposome to about 1 mg of total recombinant molecules per 8 µmol of liposome, and even more preferably from about 200 µg per 2 µmol of liposome to about 400 µg of total recombinant molecules per 3.2 µmol of liposome.

A preferred single dose of a cytokine-encoding recombinant molecule in a non-targeting carrier to administer to an animal to treat a tumor, is from about 100 µg to about 2 mg of total recombinant molecules, more preferably from about 150 µg to about 1 mg of total recombinant molecules, and even more preferably from about 200 µg to about 400 µg of total recombinant molecules. A preferred single dose of a cytokine-encoding recombinant molecule complexed with liposomes to administer to an animal to treat a tumor, is from about 100 µg of total recombinant molecules per 800 nmol of liposome to about 2 mg of total recombinant molecules per 16 µmol of liposome, more preferably from about 150 µg per 1.2 µmol of liposome to about 1 mg of total recombinant molecules per 8 µmol of liposome, and even more preferably from about 200 µg per 2 µmol of liposome to about 400 µg of total recombinant molecules per 6.4 µmol of liposome.

A preferred single dose of a superantigen-encoding recombinant molecule in a non-targeting carrier to administer to an animal treat a metastatic cancer, is from about 100 µg to about 4 mg of total recombinant molecules, more preferably from about 150 µg to about 3 mg of total recombinant molecules, and even more preferably from about 200 µg to about 2 mg of total recombinant molecules. A preferred single dose of a superantigen-encoding recombinant molecule complexed with liposomes to administer to an animal to treat a metastatic cancer, is from about 100 µg of total recombinant molecules per 800 nmol of liposome to about 4 mg of total recombinant molecules per 32 µmol of liposome, more preferably from about 200 µg per 1.6 µm of liposome to about 3 mg of total recombinant molecules per 24 µmol of liposome, and even more preferably from about 400 µg per 3.2 µmol of liposome to about 2 mg of total recombinant molecules per 16 µmol of liposome.

A preferred single dose of a cytokine-encoding recombinant molecule in a non-targeting carrier to administer to an animal to treat a metastatic cancer, is from about 100 µg to about 4.0 mg of total recombinant molecules, more preferably from about 150 µg to about 3 mg of total recombinant molecules, and even more preferably from about 200 µg to about 2 mg of total recombinant molecules. A preferred single dose of a cytokine-encoding recombinant molecule complexed with liposomes to administer to an animal to treat a metastatic cancer, is from about 100 µg of total recombinant molecules per 800 nmol of liposome to about 4.0 mg of total recombinant molecules per 32 µmol of liposome, more preferably from about 200 µg per 1.6 µmol of liposome to about 3 mg of total recombinant molecules per 24 µmol of liposome, and even more preferably from about 400 µg per 3.2 µmol of liposome to about 2 µg of total recombinant molecules per 16 µmol of liposome.

According to the present invention, a single dose of a therapeutic composition useful to treat a lesion, comprising a superantigen-encoding recombinant molecule in a non-targeting carrier or liposomes, respectively, and a cytokine-encoding recombinant molecule in a non-targeting carrier or liposomes, respectively, is substantially similar to those doses used to treat a tumor (as described in detail above).

It will be obvious to one of skill in the art that the number of doses administered to an animal is dependent upon the extent of the disease and the response of an individual patient to the treatment. For example, a large tumor may require more doses than a smaller tumor. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses includes any number required to cause regression of a disease. A preferred protocol is monthly administrations of single doses (as described above) for up to about 1 year. A preferred number of doses of a therapeutic composition comprising a superantigen-encoding recombinant molecule and a cytokine-encoding recombinant molecule in a non-targeting carrier or complexed with liposomes in order to treat a tumor is from about 1 to about 10 administrations per patient, preferably from about 2 to about 8 administrations per patient, and even more preferably from about 3 to about 5 administrations per person. Preferably, such administrations are given once every 2 weeks until signs of remission appear, then once a month until the disease is gone.

A preferred number of doses of a therapeutic composition comprising a superantigen-encoding recombinant molecule and a cytokine-encoding recombinant molecule in a non-targeting carrier or complexed with liposomes in order to treat a metastatic cancer, is from about 2 to about 10 administrations patient, more preferably from about 3 to about 8 administrations per patient, and even more preferably from about 3 to about 7 administrations per patient. Preferably, such administrations are given once every 2 weeks until signs of remission appear, then once agmonth until the disease is gone.

According to the present invention, the number of doses of a therapeutic composition to treat a lesion comprising a superantigen-encoding recombinant molecule and a cytokine-encoding recombinant molecule, in a non-targeting carrier or liposomes, respectively, is substantially similar to those number of doses used to treat a tumor (as described in detail above).

A therapeutic composition is administered to an animal in a fashion to enable expression of the administered recombinant molecule of the present invention into a curative protein in the animal to be treated for disease. A therapeutic composition can be administered to an animal in a variety of methods including, but not limited to, local administration of the composition into a site in an animal, in which the site contains abnormal cells or pathogens to be destroyed (e.g., injection locally within the area of a tumor or a lesion); and systemic administration.

Therapeutic compositions to be delivered by local administration include: (a) recombinant molecules of the present invention in a non-targeting carrier (e.g., as "naked" DNA molecules, such as is taught, for example in Wolff et al., 1990, Science 247, 1465–1468); and (b) recombinant molecules of the present invention complexed to a delivery vehicle of the present invention. Suitable delivery vehicles for local administration comprise liposomes. Delivery vehicles for local administration can further comprise ligands for targeting the vehicle to a particular site (as described in detail herein).

A preferred method of local administration is by direct injection. Direct injection techniques are particularly useful for the treatment of disease by, for example, injecting the composition into a mass formed by abnormal cells or a granuloma mass induced by pathogens. Preferably, a recombinant molecule of the present invention complexed with a delivery vehicle is administered by direct injection into or locally within the area of a tumor mass, a granuloma mass or a cancer cell. Administration of a composition locally within the area of a mass or a cell refers to injecting the composition centimeters and preferably, millimeters within the mass or the cell. A preferred tumor mass to inject includes discrete inner body and cutaneous solid tumors. A preferred inner body tumor to inject includes a discrete solid tumor that forms in the brain, breast, liver, kidney, colon, prostate, testicular, ovary, spleen and/or lymph node. A preferred cutaneous tumor to inject includes a discrete solid melanoma.

Another method of local administration is to contact a therapeutic composition of the present invention in or around a surgical wound. For example, a patient can undergo surgery to remove a tumor. Upon removal of the tumor, the therapeutic composition can be coated on the surface of tissue inside the wound or the composition can be injected into areas of tissue inside the wound. Such local administration is useful for treating cancer cells not excised by the surgical procedure, as well as, preventing recurrence of the primary tumor or development of a secondary tumor in the area of the surgery.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site, preferably ligands for targeting the vehicle to a site of a cancer or a lesion (depending upon the disease being treated). For cancer treatment, ligands capable of selectively binding to a cancer cell or to a cell within the area of a cancer cell are preferred. Systemic administration is useful for the treatment of both tumor and metastatic cancer and systemic infectious diseases. Systemic administration is particularly useful for the treatment of metastatic forms of cancer, in which the cancer cells are dispersed (i.e., not localized within a single tumor mass). Systemic administration is particularly advantageous when organs, in particular difficult to reach organs (e.g., heart, spleen, lung or liver) are the targeted sites of treatment.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

Therapeutic compositions of the present invention can be administered to any animal, preferably to mammals and birds, and more preferably to humans, house pets, economic produce animals and zoo animals. Economic produce animals include animals to be consumed or that produce useful products (e.g., sheep for wool production). Zoo animals include those animals harbored in zoos. Preferred animals to protect include humans, dogs, cats, sheep, cattle, horses and pigs, with humans and dogs being particularly preferred. While a therapeutic composition of the present invention is effective to treat disease in inbred species of animals, the composition is particularly useful for treating outbred species of animals, in particular those having tumors.

Yet another embodiment of the present invention is a method to suppress T cell activity in an animal, the method comprising administering to an animal an effective amount of a therapeutic composition comprising: (a) a naked nucleic acid molecule encoding a superantigen; and (b) a pharmaceutically acceptable carrier, in which the nucleic acid molecule is operatively linked to a transcription control sequence, and in which the therapeutic composition is targeted to a site in the animal that contains excessive T cell activity.

Suitable embodiments, single dose sizes, number of doses and modes of administration of a therapeutic composition of the present invention useful in a treatment method of the present invention are disclosed in detail herein.

A therapeutic composition of the present invention is also advantageous for the treatment of autoimmune diseases in that the composition supresses the harmful stimulation of T cells by autoantigens (i.e., a "self", rather than a foreign antigen). Superantigen-encoding recombinant molecules in a therapeutic composition, upon transfection into a cell, produce superantigens that delete harmful populations of T cells involved in an autoimmune disease. A preferred therapeutic composition for use in the treatment of autoimmune disease comprises a superantigen-encoding recombinant molecule of the present invention. A more preferred therapeutic composition for use in the treatment of autoimmune disease comprises a superantigen-encoding recombinant molecule combined with a non-targeting carrier of the present invention, preferably saline or phosphate buffered saline.

Such a therapeutic composition of the present invention is particularly useful for the treatment of autoimmune diseases, including but not limited to, multiple sclerosis, systemic lupus erythematosus, myasthenia gravis, rheumatoid arthritis, insulin dependent diabetes mellitus, psoriasis, polyarteritis, immune mediated vasculitides, immune mediated glomerulonephritis, inflammatory neuropathies and sarcoidosis.

A single dose of a superantigen-encoding nucleic acid molecule in a non-targeting carrier to administer to an animal to treat an autoimmune disease is from about 0.1 µg to about 200 µg of total recombinant molecules per kilogram (kg) of body weight, more preferably from about 0.5 µg to about 150 µg of total recombinant molecules per kg of body weight, and even more preferably from about 1 µg to about 10 µg of total recombinant molecules per kg of body weight.

The number of doses of a superantigen-encoding recombinant molecule in a non-targeting carrier to be administered to an animal to treat an autoimmune disease is an injection about once every 6 months, more preferably about once every 3 months, and even more preferably about once a month.

A preferred method to administer a therapeutic composition of the present invention to treat an autoimmune disease is by local administration, preferably direct injection. Direct injection techniques are particularly important in the treatment of an autoimmune disease. Preferably, a therapeutic composition is injected directly into muscle cells in a patient, which results in prolonged expression (e.g., weeks to months) of a recombinant molecule of the present invention. Preferably, a recombinant molecule of the present invention in the form of "naked DNA" is administered by direct injection into muscle cells in a patient.

Another apect of the present invention is an adjuvant for use with a nucleic acid-based vaccine to protect an animal from a disease, the adjuvant comprising a combination of a superantigen-encoding nucleic acid molecule and a cytokine nucleic acid molecule of the present invention. Suitable vaccines to combine with an adjuvant of the present invention include any vaccine that is administered to an animal in the form of a nucleic acid molecule to be expressed in the animal to produce a protein capable of immunizing or tolerizing the animal against a foreign agent. Suitable doses of a superantigen-encoding and a cytokine-encoding and a vaccine nucleic acid molecule can be determined by one of skill in the art using standard methods. A preferred dose includes a dose capable of producing a sufficient amount of superantigen and cytkine protein to stimulate effector cell immunity in a manner that enhances the effectiveness of the vaccine. An adjuvant of the present invention is particularly useful when administering a vaccine to a human because some traditional adjuvants can be toxic (e.g., Freund's adjuvant and other bacterial cell wall components) and others are realtively ineffective (e.g., aluminum-based salts and calcium-based salts). Preferred adjuvants of the present invention include mixtures of $PCR_3$-SEA and $PCR_3$-$GM_3$, $PCR_3$-SEA.S and $PCR_3$-$GM_3$, $PCR_3$-SEB and $PCR_3$-$GM_3$, $PCR_3$-SEB.S and $PCR_3$-$GM_3$, or $PCR_3$-TSST and $PCR_3$-$GM_3$. More preferred adjuvants include mixtures of $PCR_3$-SEB.S and $PCR_3$-$GM_3$, or $PCR_3$-SEA.S and $PCR_3$-$GM_3$, and $PCR_3$-TSST and $PCR_3$-$GM_3$.

The following examples are provided for the purposes of illustration and are not intended to limit the scope of the present invention.

EXAMPLES

Example 1

This example describes the production of recombinant molecules encoding superantigens and cytokines.

Full-length cDNA encoding *Staphylococcal enterotoxin* B (SEB; SEQ ID NO:1) and *Staphylococcal enterotoxin* A (SEA; SEQ ID NO:3) were produced by polymerase chain reaction (PCR) amplification using templates obtained from Dr. John Kappler (National Jewish Center for Immunology and Respiratory Disease, Denver, Colo.). A truncated form of SEB lacking the leader sequence, which spans base pairs 46 to 773 (referred to herein as SEB.S), was prepared by PCR amplification using the primers 5' GGGAATTCCATG-GAGAGTCAACCAG 3' (SEQ ID NO:7) and 3' GCG-GATCCTCACTTTTTCTTTGT 5' (SEQ ID NO:8). A truncated form of SEA lacking the signal sequence, which spans base pairs 46 to 751 (referred to herein as SEA.S), was prepared by PCR amplification using the primers 5' GGGAATTCCATGGAGAGTCAACCAG 3' (SEQ ID NO:9) and 5' GCAAGCTTAACTTGTATATAAATAG 3' (SEQ ID NO:10). Full-length cDNA encoding Toxic Shock Syndrome Toxin (TSST; SEQ ID NO:5) was produced by PCR amplification using a template obtained from Dr. Brian Kotzin (National Jewish Center for Immunology and Respiratory Disease, Denver, Colo.), using the primers:

5' CGGGGTACCCCGAAGGAG-GAAAAAAAAATGTCTACAAAC-GATAATATAAAG 3' (SEQ ID NO:11); and

3' TGCTCTAGAGCATTAATTAATTTCTGCT-TCTATAGTTTTTAT 5' (SEQ ID NO:12).

Each cDNA clone was ligated into the eukaryotic expression vector $PCR_3$ (In Vitrogen, San Diego, CA) using standard cloning methods. The full-length SEB cDNA cloned into $PCR_3$ is referred to herein as $PCR_3$-SEB; the full-length SEA cDNA cloned into $PCR_3$ is referred to herein as $PCR_3$-SEA; the full-length TSST cDNA cloned into $PCR_3$ is referred to herein as $PCR_3$-TSST; the truncated SEB cDNA cloned into $PCR_3$ is referred to herein as $PCR_3$-SEB.S; and the truncated SEA cDNA cloned into $PCR_3$ is referred to herein as $PCR_3$-SEA.S.

A cDNA for canine GM-CSF was produced by PCR amplification of total RNA extracted from Concavalin A-stimulated normal canine peripheral blood mononuclear cells (PBMC) using canine GM-CSF primers designed based on the published canine GM-CSF cDNA (Nash, ibid.). The total RNA was reverse transcribed using the reverse transcriptase enzyme and oligoT primers. The canine GM-CSF cDNA was then amplified using PCR and specific 5' and 3' primers. The PCR product was cloned into the $PCR_3$ vector, the resulting recombinant molecule is referred to herein as $PCR_3$-$GM_3$.

Example 2

This example describes the expression of DNA encoding superantigens in mammalian CHO cells following transfection.

Isolated PCR$_3$-SEB.S, PCR$_3$-SEA.S and PCR$_3$-TSST were transformed into *E. coli* cells and ampicillin-resistant bacterial colonies were screened for the presence of the plasmid. Selected colonies were then cultured in large scale culture (liter volume). Plasmid DNA was isolated using standard methods. A typical plasmid yield was 20 mg plasmid DNA from one liter of bacteria-containing culture medium. Plasmid DNA was transfected into Chinese hamster ovary cells (CHO) by lipofection (Lipofectamine, Gibco-BRL, Gaithersburg, MD) using methods provided by the manufacturer. About 2.0 µg of each plasmid DNA was separately transfected into about $10^6$ CHO cells.

The transfected CHO cells were cultured for 48 hours. Supernatants and cell lysates were then isolated to determine the amount of intracellular and secreted SAg protein produced by the transfected cells. Cell lysates were prepared by detaching and sonicating the transfected cells to prepare cell lysates to measure activity. SAg protein activity in each sample was measured by quantitating the ability of the SAg protein to stimulate lymphocyte contained in a PBMC population using the following method. Supernatants and lysates to be tested were added in serial dilutions to triplicate wells of a 96-well plate containing $5 \times 10^5$ PBMC in a total volume of 200 µl per well. After 3 days, the wells were pulsed with $^3$H thymidine and incubated for 18 hours. The radioactivity incorporated into the PBMC's were counter. Nd on a beta counter. Negative controls included CHO cells transfected with the DNA vector without an inserted gene (mock) and positive controls were purified recombinant SAg proteins.

The results were plotted as the mean incorporated thymidine in counts per minute and are shown in FIG. 1. The results indicate that both supernatants and lysates of CHO cells transfected with PCR$_3$-SEB.S, PCR$_3$-SEA.S and PCR$_3$-TSST stimulated strong proliferation of the PBMC's, compared to mock transfected cultures. The activity in supernatants in some cases exceeded that in cell lysates. Thus, DNA encoding bacterial SAg proteins are capable of being transcribed and translated in mammalian cells in biologically active form. The results also indicate that the amounts of biologically active SAg protein are active produced by the transfected cells was sufficient to stimulate T cell proliferation.

Example 3

This example describes the expression of DNA encoding superantigens in canine melanoma cells following transfection.

Figure 2:
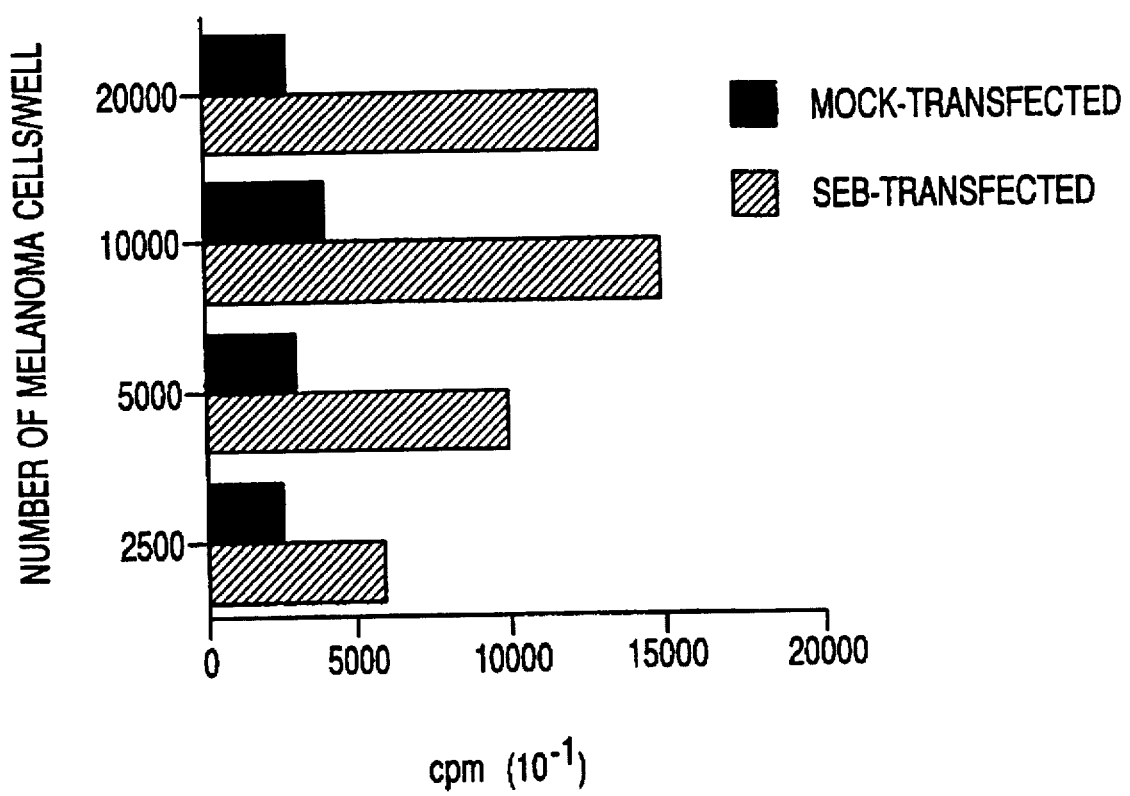
FIG. 2 illustrates the proliferative response of canine PBMC's to canine melanoma cells transfected with a superantigen-encoding DNA plasmids.

A melanoma cell line was established from an oral malignant melanoma obtained by biopsy from a canine patient by isolating a portion of a melanoma tumor, digesting that portion with collagenase and plating the released cells in 24 well plates using Iscove Modified Dulbecco's Medium (IMDM) with 10% fetal calf serum. Melanoma cells were transfected with PCR$_3$-SEB.S, PCR$_3$-SEA.S and PCR$_3$-TSST by lipofection as described in Example 2. The cells were then irradiated (15,000 Rads). Four samples of each sample of transfected melanoma cells were prepared, in which decreasing numbers of the transfected cells were added to normal canine PBMC ($5 \times 10^5$/ well). Each sample was prepared in triplicate in a 96 well plate. After 3 days, proliferation was quantitated as described in Example 2. Non-transfected melanoma cells were used as negative control samples. The results were plotted as the mean incorporated thymidine in counts per minute and are shown in FIG. 2. The results indicate that Canine PBMC proliferated when cultured with canine melanoma cells transfected with PCR$_3$-SEB.S, PCR$_3$-SEA.S and PCR$_3$-TSST, exhibiting a dose-dependent increase in proliferation as increasing numbers of irradiated tumor cells were used. Thus, melanoma tumor cells can be transfected and can express biologically active SAg protein. The results also show that the transfected melanoma cells continue to release biologically active SAg protein after irradiation, indicating that transfected tumor cells would also be useful as an autologous tumor vaccine as described in detail in the present application.

Example 4

This example describes the long term expression of DNA encoding SEB.S and SEA.S in stably transfected CHO cells.

To determine whether the SAg protein activity detected in supernatants of transfected CHO cells (described in Example 2) represented actual secretion or simple release from dying cells, stably transfected CHO lines were prepared using either PCR$_3$-SEB.S, PCR$_3$-SEA.S or vector with no cDNA insert (control). About $2 \times 10^6$ CHO cells were transfected with about 2 µg of plasmid DNA by lipofection. The transfected cells were then cultured in G418 (1 mg/ml) for 3 weeks to obtain stable transfectants. The G418 selected CHO cells were seeded into 9 individual tissue culture wells, allowed to adhere for 4 hours, and then fresh tissue culture media was added. Supernatants were harvested sequentially, beginning at time zero and continuing for 36 hours. Supernatants were added to PBMC to assay for SAg protein activity, as described in Example 2.

Figure 3A:
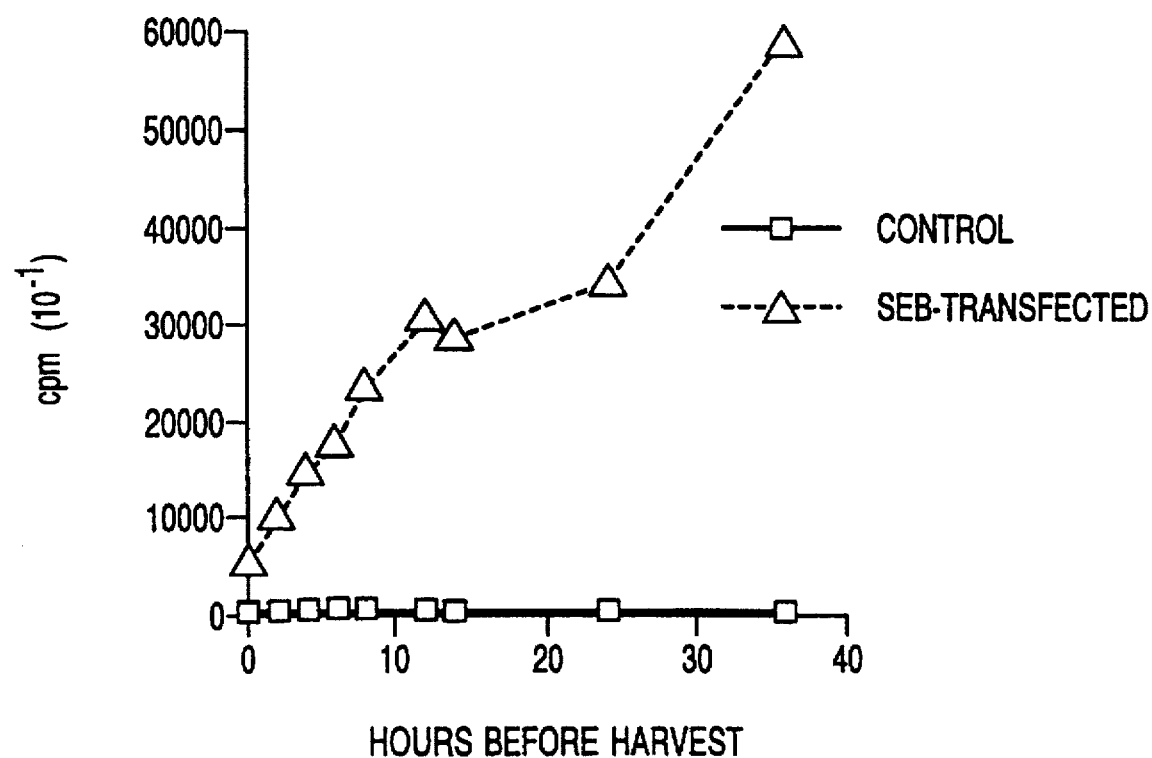
FIGS. 3A and 3B illustrate the release of superantigen protein by CHO cells transfected with superantigen-encoding DNA plasmids.
Figure 3B:
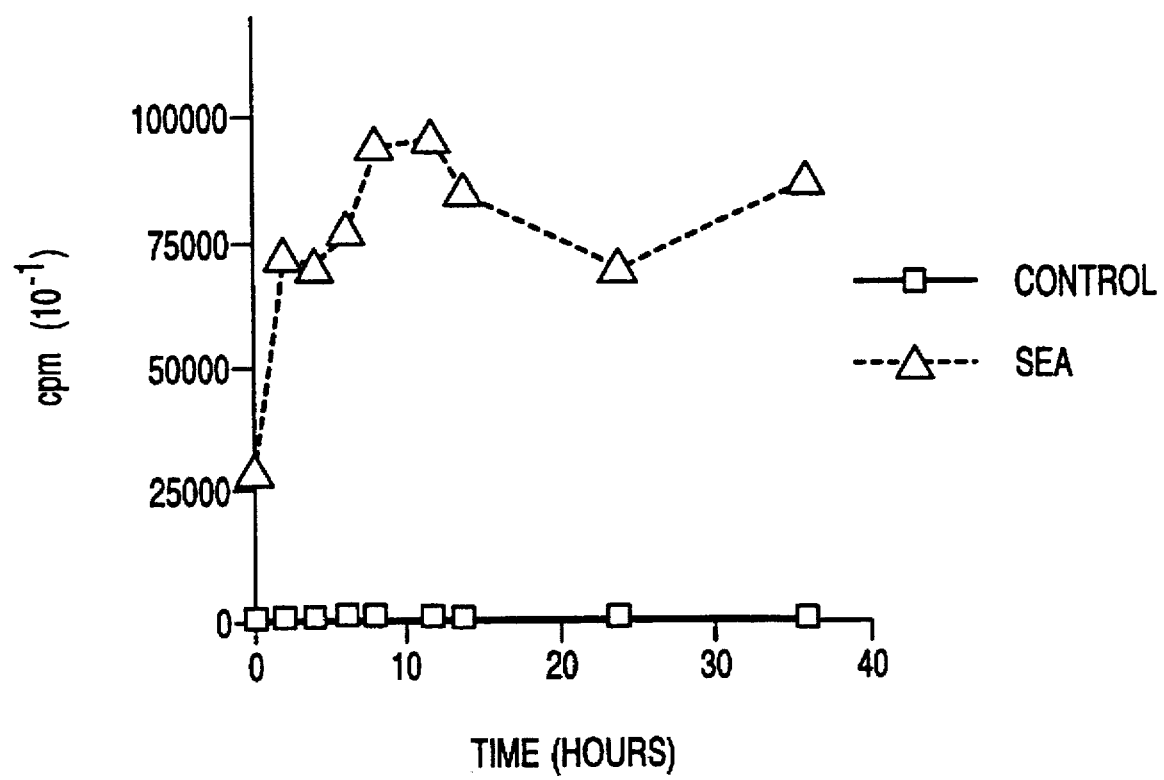

The results were plotted as the mean proliferation stimulating activity contained in supernatants at each time point and are shown in FIGS. 3A and 3B. The results indicate that a steady time-dependent increase in PBMC stimulatory activity was observed in supernatants from CHO cells stably transfected with both PCR$_3$-SEB.S and PCR$_3$-SEA.S. Thus, transfection of mammalian cells with PCR$_3$-SEB.S, PCR$_3$-SEA.S results in long term expression of biologically active SAg protein. The data indicates that transfected mammalian cells can serve as a sustained source of SAg protein production.

Example 5

This example describes that transfection of PCR$_3$-SEA.S DNA in melanoma cells results in the expression of biologically active SEA.S protein.

Superantigens are capable of stimulating the proliferation of T cells bearing certain Vβ domains in their T cell receptor (TCR). SEA is known to stimulate T cells having a Vβ3+ TCR in mice. SEB does not stimulate Vβ3+ T cells. Therefore, an experiment was performed to assess the ability of SEA.S protein expressed by melanoma cells transfected with PCR$_3$-SEA.S DNA to stimulate the proliferation of a T cell clone (AD10) expressing the V B3+TCR.

B16 melanoma cells were transfected with PCR$_3$-SEA.S DNA, PCR$_3$-SEB.S or PCR$_3$ vector DNA with no insert (mock). The cells were then irradiated (18,000 Rads) and plated in triplicate in a 96 well plate at a concentration of about $1 \times 10^4$ per well. About $1 \times 10^5$ AD10 cells were added to each well. Next, irradiated syngeneic spleen cells were added to each well as a source of antigen presenting cells for the superantigen and T cell interaction. Negative controls included mock transfected cells; positive controls included recombinant SEA (10ng/ml). The cells were incubated for 48 hours. $^3$H thymidine was then added to each well and the proliferative response quantitated.

Figure 4:
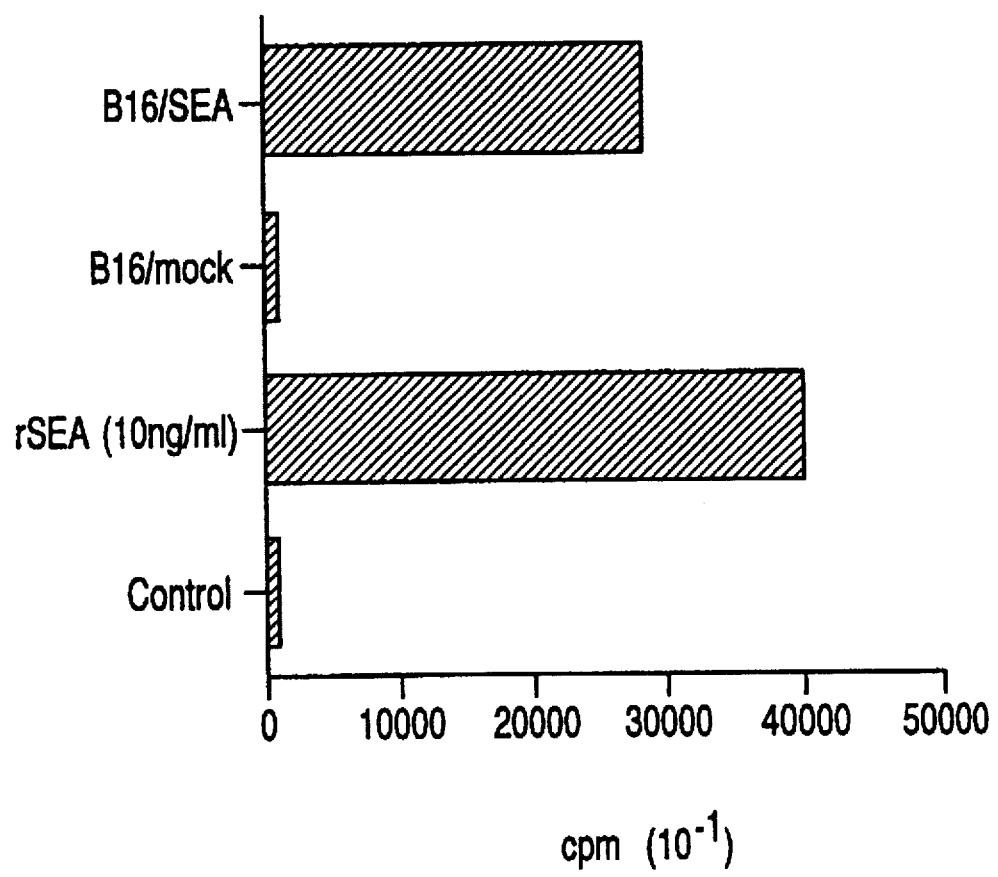
FIG. 4 illustrates the proliferative response of the Vβ3+ T cell clone AD10 to melanoma cells transfected with superantigen-encoding DNA plasmid.

The results were plotted as the mean incorporated thymidine in counts per minute and are shown in FIG. 4. The AD10 cells proliferated strongly in response to SEA.S protein produced by the PCR$_3$-SEA.S DNA transfected into the B16 cells, with the proliferative response nearly equal to that of the recombinant protein. Thus, the T cell response generated by transfection of melanoma cells with PCR$_3$-SEA.S DNA is specific for the correct TCR. Cells transfected with PCR$_3$-SEB.S DNA did not stimulate proliferation of AD10 cells, consistent with the predicted TCR specificity of SEA and SEB.

Example 6

This example describes the expression of PCR$_3$-GM DNA in CHO cells.

PCR$_3$-GM DNA was produced, isolated and transfected into CHO cells using the methods described in Examples 1 and 2. Expression of GM-CSF protein in the CHO cells was measured by the following method. Supernatants were isolated from the cultures of the transfected cells and non-transfected CHO cells. The supernatants were added to cultures of monocyte cells (obtained from normal canine PBMC) and the ability of the supernatants to support the growth and survival of monocytes was determined. After 4 days in culture with test or control CHO supernatants, monocyte survival was quantitated by addition of methyltetrazolium dye (MTT) that is reduced in viable cells. Absorbance of light at 570 nm (measured using an ELISA reader) is representative of cell survival.

Figure 5:
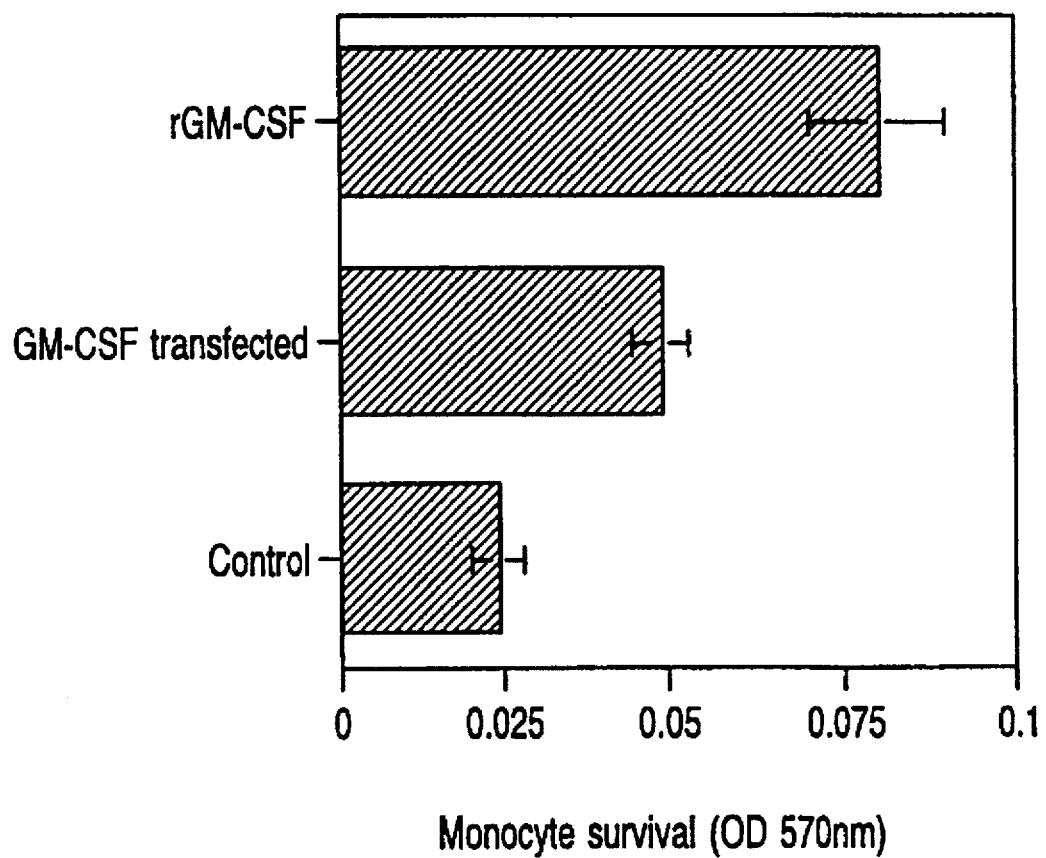
FIG. 5 illustrates the release of canine GM-CSF by CHO cells transfected with GM-CSF-encoding DNA plasmid.

The results are shown in FIG. 5 and indicate that the supernatants from CHO transfected with PCR$_3$-GM DNA stimulated the survival of canine monocytes in culture compared with results obtained using the control supernatants. The level of activity was comparable to that of $1\times10^5$ units of canine recombinant GM-CSF. Thus, the GM-CSF protein produced by CHO cells transfected with PCR$_3$-GM DNA is biologically active.

Example 7

This example demonstrates that the vaccination of mice with autologous tumor cells transfected with PCR$_3$-SEA.S DNA or PCR$_3$-SEB.S DNA induce strong cytotoxic T cell (CTL) activity.

The following experiment studies the ability of non-immunogenic murine melanoma cells (B16 melanoma cells, F10 clone) expressing either PCR$_3$-SEA.S DNA or PCR$_3$-SEB.S to induce CTL responses in mice. B16 cells are known to be non-immunogenic when injected into C57B16/J mice. The level of CTL responses that can be induced has been shown to correlate with the ability of the immunized animal to reject tumors.

B16 cells were transfected with either PCR$_3$-SEA.S DNA, PCR$_3$-SEB.S or PCR$_3$ DNA lacking insert (mock) using the method described in Example 2. The cells were then irradiated at 12,000 Rads. About $10^6$ irradiated cells were then injected subcutaneously into C57B16/J mice. Three weeks later, the mice were sacrificed and their spleen mononuclear cells harvested. Mononuclear cells isolated from the spleen cells were then restimulated in vitro with irradiated, non-transfected wild type B16 cells for 6 days in media with interleukin-2 (IL-2). The spleen cells were then added in decreasing numbers to about $5\times10^3$ of $^{51}$Cr-labeled wild type (non-transfected) B16 cells in a standard chromium release assay for CTL activity. After 4 hours, the supernatants were harvested and the percentage of specific lysis of the target B16 melanoma cells was quantitated.

Figure 6A:
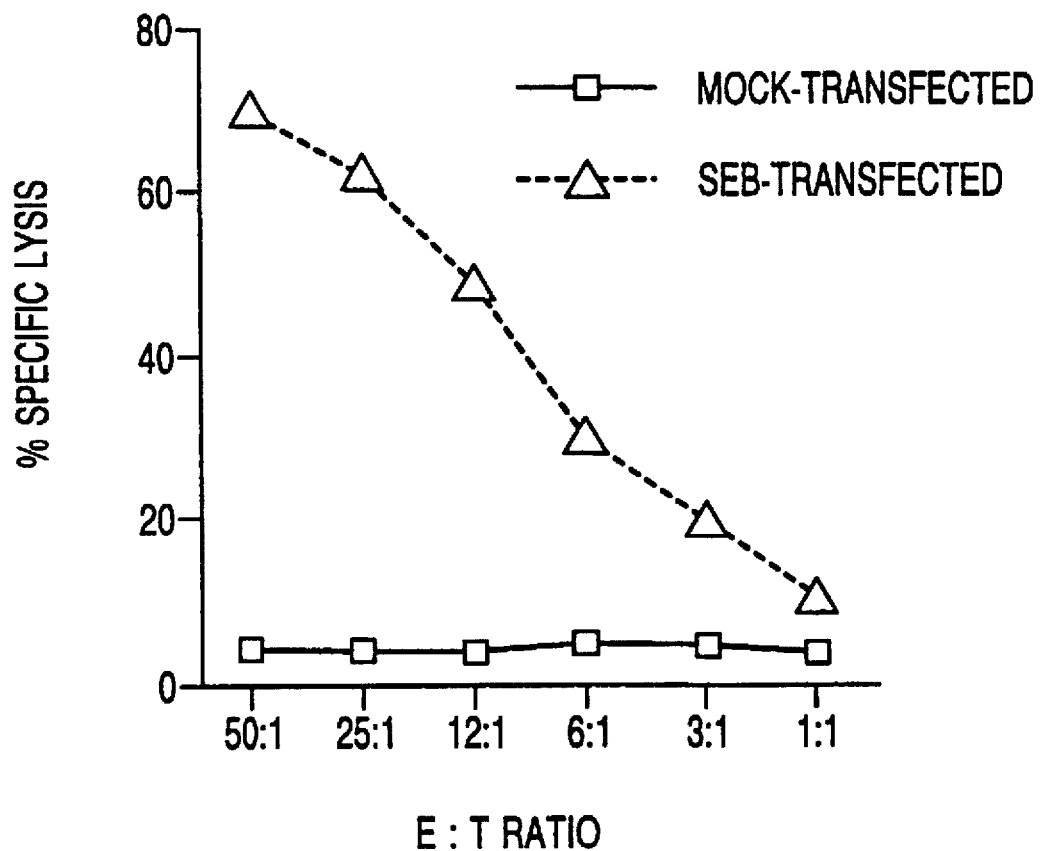
FIGS. 6A and 6B illustrate the vaccination of mice with autologous tumor cells transfected with superantigen-encoding DNA plasmid.
Figure 6B:
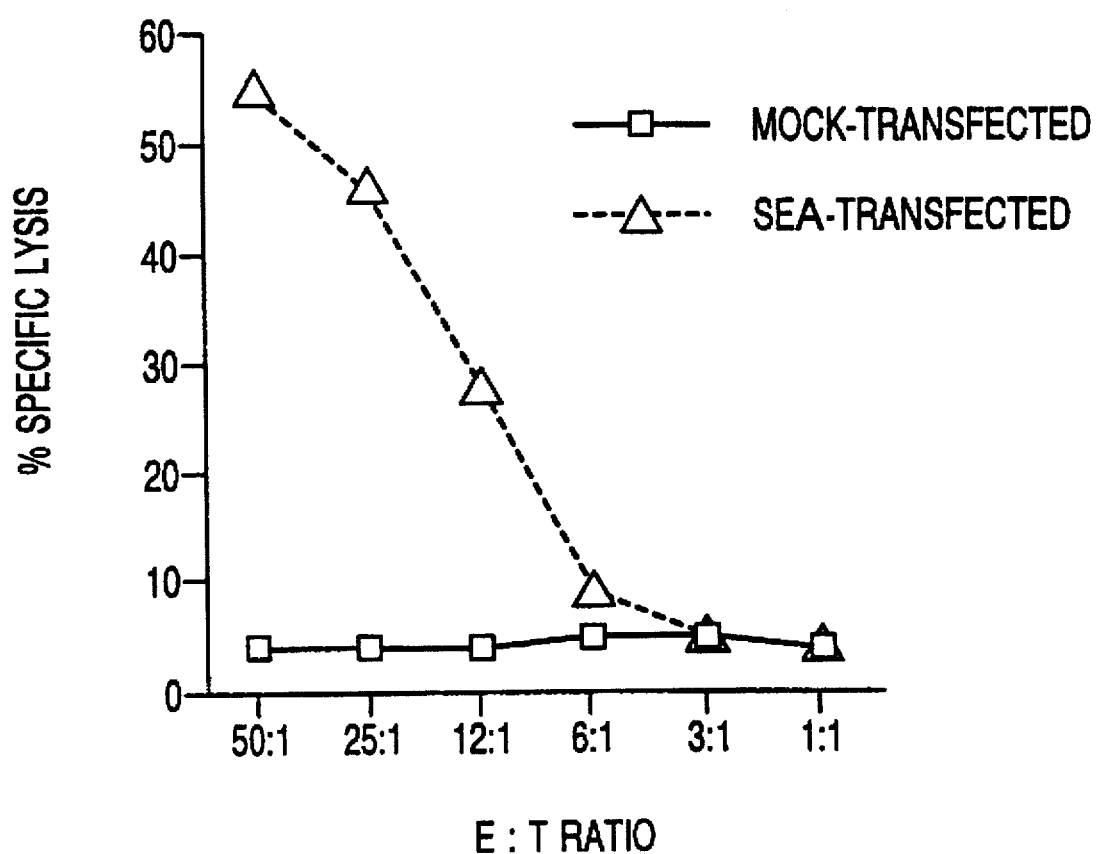

The results are shown in FIGS. 6A and 6B and indicate that injection of animals with irradiated transfected melanoma cells induce greater CTL activity than injection with non-transfected cells. This result is consistent with the non-immunogenic nature of B16 cells. Thus, DNA encoding bacterial SAg proteins expressed in transfected tumor cells are capable of eliciting strong CTL-mediated immunity against the non-transfected parental cell. These results suggest that autologous tumor cells trasnfected wiht DNA encoding a superantigen constitute an effective tumor vaccine for treatment or prevention of metatastic disease.

Example 8

This example demonstrates that tumor cells transfected with PCR$_3$-SEB.S DNA are capable of inducing cytotoxic activity in adjacent T cells.

T cells were prepared from a mouse immunized with non-transfected B16 cells using the methods described in Example 7. These isolated cells exhibited minimal CTL activity towards non-transfected B16 target cells. B16 cells were transfected with PCR$_3$-SEB.S using the methods generally described in Example 2. Induction of CTL activity by the transfected B16 target cells was assessed in a standard 4 hour chromium release assay as used in Example 7.

Figure 7:
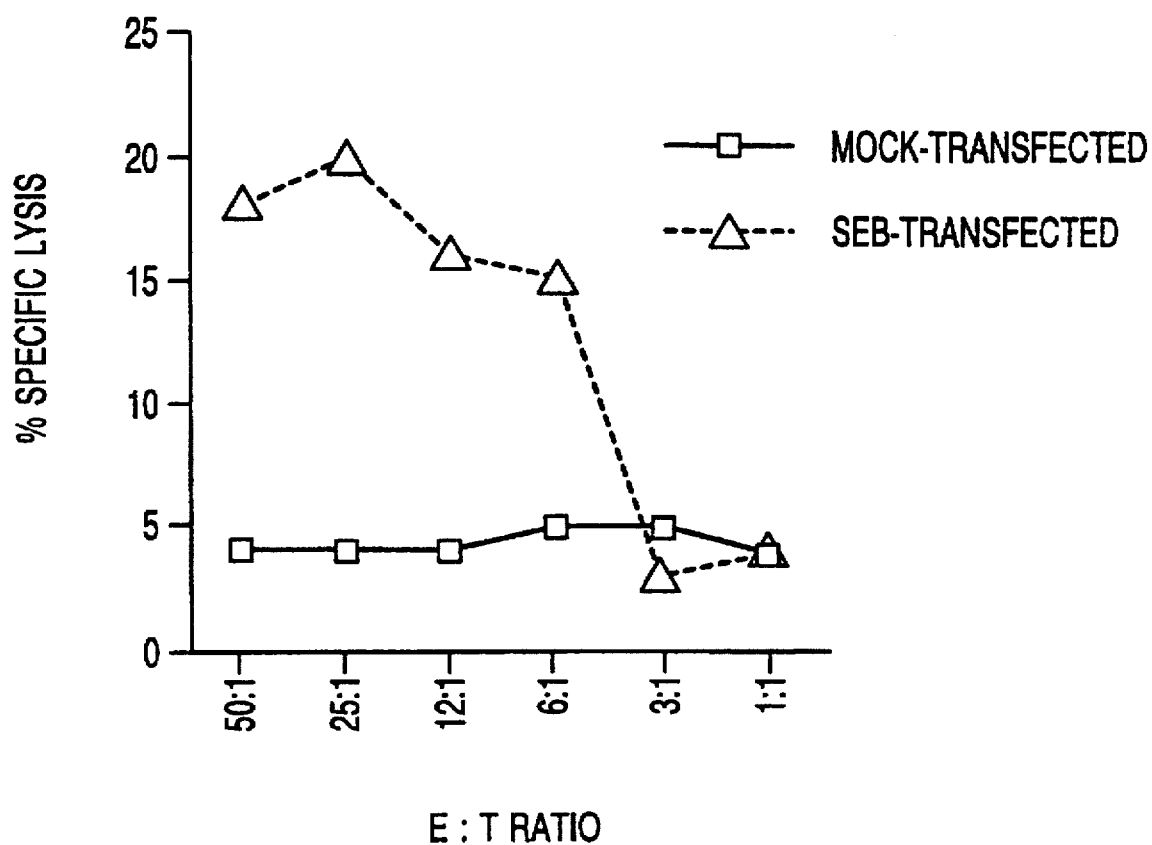
FIG. 7 illustrates the effect of tumor target transfection on cytotoxic T cell lysis.

The results are shown in FIG. 7 and indicates that B16 cells transfected with PCR$_3$-SEB.S produced protein that rapidly induced a four-fold increase in CTL activity in T cells that were relatively unresponsive to non-transfected target B16 cells. Thus, the SEB produced in the vicinity of the isolated T cells by the B16 cells is capable of stimulating such T cells. The data indicates that tumor cells transfected in vivo with PCR$_3$-SEB.S can produce biologically active SEB.S that is capable of rapidly activating T lymphocytes in their vicinity and thereby inducing cytotoxic activity against themselves or neighboring tumor cells.

Example 9

This example describes the treatment of canine melanoma with DNA encoding superantigen or GM-CSF.

A. Criteria for entry and trial design Animals selected for entry into the present study were client owned animals with spontaneous oral malignant melanoma, a highly malignant neoplasm of dogs for which there is no alternative effective treatment. Prior to entry, the owners were required to sign informed consent. The study consisted of an initial 12 week trial response phase with 6 injections given once every 2 weeks, followed by long term once monthly maintenance therapy for those animals that responded during the initial 12 week induction phase. Potential toxicity was assessed by (1) body temperature measured daily for 7 days after injection; (2) physical examination of the injection site; (3) owner's assessment of their pet's attitude and appetite; (4) complete blood counts and biochemistry measurements once monthly. Treatment responses were assessed by: (1) physical measurement of tumor dimensions; (2) tumor photography; (3) thoracic radiographs for metastasis evaluation.

B. Superantigen+GM-CSF Treatment protocol

DNA samples complexed with liposomes were prepared as follows. PCR$_3$-SEB.S and PCR$_3$-GM plasmid DNA prepared from bacterial cultures by the alkaline lysis method, then purified by CsCl banding, were resuspended at a 1.0 mg/ml concentration in sterile PBS. Liposomes were prepared by mixing equimolar amounts of N-[1-(33-dioleyloxy)propyl]-N,N,N-triethylammonium (DOTMA; obtained from Syntex, Corp., Palo Alto, Calif.) and dioleoyl phosphatidylethanolamine (DOPE; obtained from Avanti Polar Lipids, Birmingham, AL). The lipids were dried in a dessicator and reconstituted at a concentration of 1.0 mg/ml in sterile phosphate buffered saline (PBS), pH 7.0. The reconstituted lipids were sonicated for 5 minutes to produce liposomes having an average size of about 200 nm to about 400 nm.

Thirty minutes prior to injection into the patients, the PCR$_3$-SEB.S and PCR$_3$-GM DNA was mixed with the liposomes at a ratio of 1.0 µg DNA to 4 nmol liposome, in 1.0 ml sterile PBS. The solution was allowed to complex at room temperature. Two doses of DNA were administered, depending on tumor volume. For tumors less than 3 centimeters (cm) in diameter, 400 µg total DNA (200 µg each of PCR$_3$-SEB.S and PCR$_3$-GM DNA) were injected into each tumor. For tumors larger than 3 cm diameter, a total of 800 µg DNA (400 µg each of PCR$_3$-SEB.S and PCR$_3$-GM DNA) were injected into each tumor.

For each treatment, the DNA:liposome mixture was injected into the tumor site with a 3 ml syringe and 25 gauge needle. For larger tumors, most of the injection was delivered into tissues at the periphery of the tumor base. For some smaller tumors, injections were also injected directly into tumor tissue. Lymph node tissue having evidence of tumor metastasis was also injected. Injections were performed once every 2 weeks for the first 12 weeks, then continued twice monthly for those animals in which an initial treatment response occurred, until complete tumor regression occurred. At that time, the frequency of injections decreased to once monthly. The toxicity of the treatment was evaluated based on the parameters outlined above in section A. The results are shown below in Table 1.

12 week trial. On average, a tumor response required 6 to 10 weeks to become apparent. The injections did not cause any inflammation or necrosis at injections sites. Toxicity, either local or systemic, was not observed in any of the 10 patents treated in this study. These results provide evidence of the efficacy of direct DNA injection using DNA encoding superantigen (SEB) and cytokine (GM-CSF) for treatment of spontaneous malignant melanoma in an outbred species.

Canine melanoma is a highly malignant, rapidly growing tumor of dogs, and provides a useful model for the study of treatments for human melanoma. Without treatment, the 50% survival time for animals with stage III disease (5 of the patients in this study) is about 3 months and all animals will be dead by 5 months due to pulmonary metastases. The observation of several long term survivors shown in Table 1 (others have not been treated long enough to evaluate) suggests that the combined DNA immunotherapy approach also has a systemic effect on preventing metastasic diseases.

Another major advantage of this approach is the apparent complete absence of toxicity in the dogs. Since dogs respond to SAg protein similar to humans, it is also likely that toxicity in humans would also be minimal. The delivery of DNA encoding superantigens into tumor cells by transfection and subsequent local expression is sufficient to induce a strong immune response without inducing toxicity. Thus this genetic approach to tumor immunotherapy offers advantages over conventional chemotherapy and radiation therapy in terms of reducing patient morbidity. In addition, delivering the SAg protein by DNA transfection also avoids the potential toxicity associated with systemic administration.

C. Single Gene Treatment Protocol

To evaluate the effectiveness of injecting DNA encoding either a superantigen or a cytokine, relative to combined genetic therapy (SAg-encoding DNA and cytokine-encoding DNA), 2 groups of dogs were treated with either PCR$_3$-SEB.S DNA alone (3 dogs) or PCR$_3$-GM DNA alone (3

TABLE 1

Patient Log for SEB.S and PCR$_3$-GM DNA Treatment of Canine Melanoma

| Patient | Stage | TN | Tumor Size | Start Date | Response | Comments |
|---|---|---|---|---|---|---|
| Zomax | I | T1bNOMO | 1.5 cm diam | 5/16/94 | CR 51 wks | SEB.S + GM-CSF |
| Shadow | III | T2bN1bMO | 3 cm diam | 5/23/94 | CR 50 wks | SEB.S + GM-CSF |
| NG | I | T1NOMO | 1.2 cm diam | 9/12/94 | CR 34 wks | SEB.S + GM-CSF |
| Maggie | II | T2aNOMO | 2 cm diam | 8/24/94 | PR 33 wks | SEB.S + GM-CSF |
| K. C. | III | T3aNOMO | >4 cm diam | 10/13/94 | SD 12 wk | SEB.S + GM-CSF |
| Belvedere | III | T2N1bMO | 4 cm diam | 10/13/94 | CR 30 wks | SEB.S + GM-CSF |
| Nicholas | III | T3bNOMO | >4 cm diam | 2/15/95 | SD 12 wks | SEB.S + GM-CSF |
| Heidi | III | TON1bMO | LN: 2 cm diam | 2/27/95 | PR 10 wks | SEB.S + GM-CSF |
| Bear | III | TON1bMO | LN: 2.5 cm | 4/11/95 | SD 4 wks | SEB.S + GM-CSF |

Key to terminology in patient data sheets:
Stage: I represents the smallest and III the largest size, with metastases
TNM: World Health Organization staging system
SD = stable disease (no tumor growth)
PR = partial remission (>50% decrease in tumor size)
CR = tumor completely regressed
PD = progressive disease, no response to treatment
MCT = mast cell tumor
Mammary CA = mammary gland adenocarcinoma (malignant breast cancer)
Thyroid CA = thyroid adenocarcinoma
SCC = squamous cell carcinoma The results shown in Table 1 indicate that a treatment response was observed in 6 of 9 dogs treated for the 12 week trial period. This included 4 complete remissions (no residual tumor) and 2 partial remissions (greater than 50% reduction in tumor size). Tumors in the remaining two dogs did not regress, but also did not progress in size during the dogs; 2 entered, one evaluable). Similar criteria for entry and trial design described above in Section A of this example was applied. Although not formally randomized, after the first 10 dogs were treated with the 2 gene combination, the next 3 enrollees were assigned the PCR$_3$-SEB.S DNA alone group and the next 3 to the PCR$_3$-GM DNA alone group. A similar treatment protocol as described above in section B was applied in this study. Briefly, the DNA was complexed with liposomes and injected once every 2 weeks for the first 12 weeks, then continued twice monthly for those animals in which an initial treatment response occurred, until complete tumor regression occurred. The toxicity of the treatment was evaluated based on the parameters outlined above in section A. The results are shown below in Table 2.

described above in Example 2. The dogs were treated initially once every 2 weeks for 12 weeks, then continued twice monthly for those animals in which an initial treatment response occurred. The toxicity of the treatment was evaluated based on the parameters outlined above in Example 9, section A. The results are shown below in Table 3.

TABLE 2

Patient Log for SEB.S or PCR₃-GM DNA alone Treatment of Canine Melanoma

| Patient | Stage | TN | Tumor Size | Start Date | Response | Comments |
|---|---|---|---|---|---|---|
| Jessie | II | T2bNOMO | 2 cm diam | 1/11/95 | PD 17 wks | SEB.S alone |
| Mr. T | III | TON1bMO | LN: 2 cm diam | 2/1/95 | PD 14 wks | SEB.S alone |
| Duffy | II | T2aNOMO | 2 cm diam | 2/3/95 | PD 12 wks | SEB.S alone |
| Scooter | I | T2aNOMO | 2 cm diam | 3/24/95 | PD 7 wks | GM-CSF alone |

The results indicated that a tumor response did not occur in any dog receiving PCR₃-SEB.S DNA alone and tumors grew progressively. In addition, one dog (Scooter) treated with PCR₃-GM DNA alone also exhibited progressive growth. These data indicate that treatment with PCR₃-SEB.S DNA alone or PCR₃-GM DNA alone does not induce tumor regression. The data indicate that the marked anti-tumor efficacy of direct DNA injection results from the combined expression of PCR₃-SEB.S DNA and PCR₃-GM DNA in a tumor and adjacent tissues.

TABLE 3

Patient Log for SEB.S and PCR₃-GM DNA Treatment of Various Carcinomas

| Patient | Tumor Type | Stage | TN | Tumor Size | Start Date | Response | Comments |
|---|---|---|---|---|---|---|---|
| Emma | Mammary CA | III | T4N1bNMO | 1.8 cm diam | 8/11/94 | PR 22 wks | SEB.S + GM-CSF |
| Baby | Mammary CA | II | T1aN1bMO | 2.6 cm diam | 9/12/94 | PR 8 wks | SEB.S + GM-CSF |
| Christa | MCT | IIIa | NA | >2 cm diam | 7/27/94 | SD 39 wks | SEB.S + GM-CSF |
| Jack | MCT | IIIa | NA | >3 cm diam | 3/28/95 | PD 4 wks | SEB.S + GM-CSF |
| Britt | Thyroid CA | III | T3bNOMO | >7 cm diam | 10/14/94 | SD 16 wk | SEB.S + GM-CSF |
| Duncan | Melanoma Toe | NA* | T2N1MO | >4 cm diam | 8/11/94 | SD 20 wks | SEB.S + GM-CSF |
| Billy | Melanoma Toe | NA* | TON1bMO | LN 3.5 cm | 1/10/95 | CR 17 wks | SEB.S + GM-CSF |
| Scotche | SCC Tonsil | NA | T3NOMO | 4 cm diam | 3/27/95 | SD | SEB.S + GM-CSF |

*Metastases
NA Not Applicable
CA Carcinoma
MCT Mast Cell Tumor
SCC Squamous Cell Carcinoma

Example 10

This example describes the treatment of various tumor types with superantigen or GM-CSF encoding DNA.

The efficacy and lack of toxicity of PCR₃-SEB.S DNA and PCR₃-GM DNA was determined for the treatment of dogs with malignancies having similar biological and histological characteristics as human cancers. Dogs with five different cancers (advanced mammary carcinoma, mast cell tumor, thyroid carcinoma, non-oral melanoma, and squamous cell carcinoma) were treated in this study. Animals selected for entry into the present study included dogs with spontaneous malignancies that had received alternative treatments (e.g., chemotherapy and/or surgery) and either, had not responded, or had relapsed.

Therapeutic samples were prepared and injected intratumorally with PCR₃-SEB.S DNA and PCR₃-GM DNA as In this study, toxicity was not observed in any of the animals. Tumor responses (partial remission of the primary tumors) were observed in the animals with mammary carcinoma and neither animal developed additional metastatic disease during the course of the study. Treatment of one dog (Billy) with a large, metastatic (lymph node metastases), non-oral melanoma resulted in complete remission of the cancer. Treatment of the other dog (Duncan) with a large, metastatic (lymph node metastases), non-oral melanoma resulted in prolonged stabilization of the disease. The dog with thyroid cancer (Britt) also experienced prolonged stabilization of the disease with once monthly injections. The response rate for the dogs with mast cell tumors was low. The effectiveness of the treatment on the squamous cell carcinoma is in early stages of evaluation. Taken together, the results indicate that PCR₃-SEB.S DNA and PCR₃-GM DNA can effectively treat multiple tumor types, in addition to the melanomas reported above in Example 9.

Example 11

This example describes the injection of PCR₃-SEA.S DNA into muscle cells which induces potent, long-lasting T cell deletion.

Four groups of mice B10.BR (2–3 mice per group) were prepared as follows. Group (1) consisted of untreated mice (control mice). Group (2) consisted of mice injected intraperitoneally with 100 ng of recombinant SEA (rSEA) protein. Group (3) consisted of mice injected intramuscularly with 100 μg of PCR$_3$-SEA.S DNA (50 μg per leg, total of 100 μg/mouse). Group (4) consisted of mice injected intramuscularly with 100 μg PCR$_3$ (no insert; mock) DNA (50 μg per leg, total of 100 μg/mouse). The DNA samples were prepared by diluting 100 μl of a solution containing 100 μg of DNA 50:50 (v:v) in sterile PBS prior to injection. The rSEA protein was purified from cultures of E. coli cells transformed with the recombinant molecule PKK223 (obtained from Dr. John Kappler) encoding the truncated SEA.S protein lacking a leader sequence.

Beginning 72 hours after injection, mice were tail bled and PBMC prepared for fluorescence activated cell sorter (FACS) analysis. Cells were double labeled with the monoclonal antibodies FITC conjugated-GK1.5 antibody, biotinylated-KJ25 antibody and biotinylated-F23.1, to analyze for expression of CD4, TCR Vμ3 and TCR Vμ8 expression, respectively. The labelled cells were analyzed on an EPICS-C flow cytometer.

The percentage of cells isolated from the experimental mice expressing CD4 that also expressed either Vβ8 or Vμ3 was calculated and compared to percentages expressed by cells isolated from control mice. The mean percentage of CD4+ and Vμ3+ T cells in PBMC was plotted against time after injection.

Figure 8:
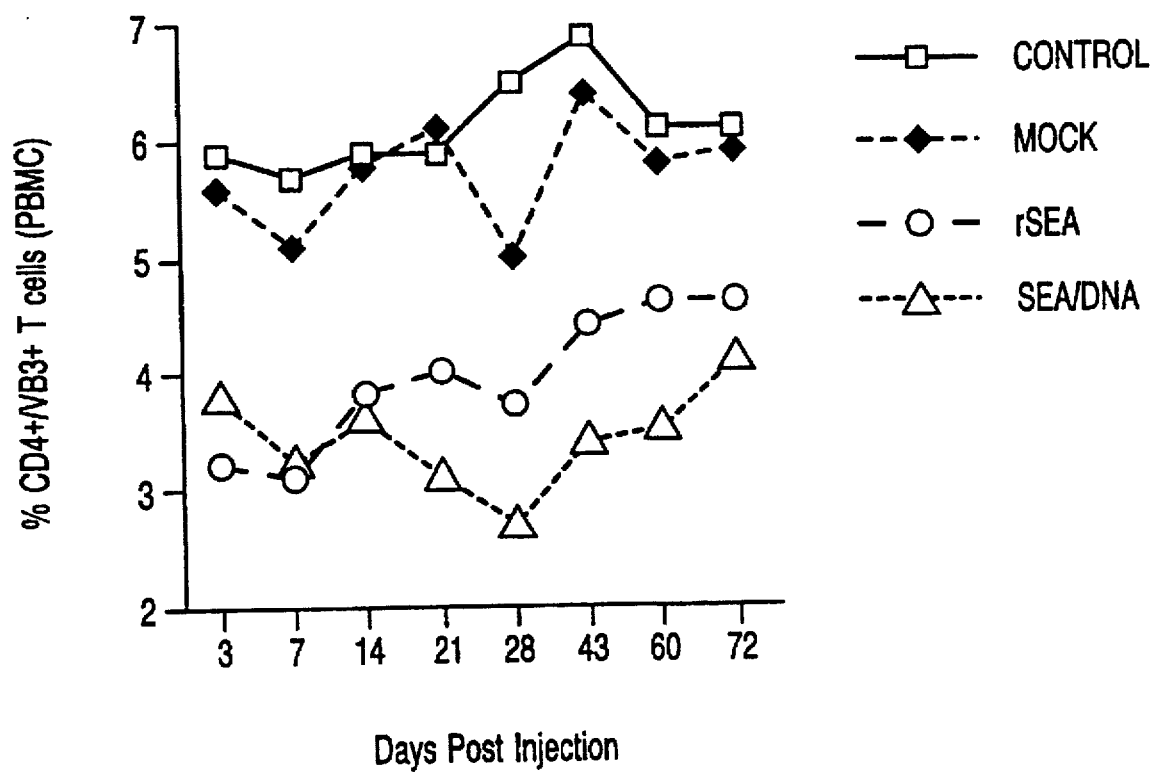
FIG. 8 illustrates the response of Vβ3+ T cells to intramuscular injection of a superantigen-encoding DNA plasmid.

The results are shown in FIG. 8 and indicate that the percentage of CD4+, Vμ3+ T cells declined rapidly in PBMC of mice that received intramuscular injections with PCR$_3$-SEA.S DNA, but not in mice mock injected with mpercentages ofpercentages of Vμ8+cells was not affected. This result is predicted since SEA protein does not bind mouse Vμ8+ T cells. The decline of the percentage of CD4+, Vμ3+T cells occurred as rapidly as in mice injected with the recombinant SEA protein (rSEA). The deletion, however, observed over the next 2 months in mice injected with PCR$_3$-SEA.S DNA was longer lasting and was more pronounced than the deletion induced by injection of SEA.S protein. In addition, injection of as little as 2 μg PCR$_3$-SEA.S DNA also induced deletion of Vμ3+ T cells. Thus, intramuscular injection of DNA encoding superantigens represents a potent and non-toxic approach to the deletion or suppression of potentially harmful (e.g., autoreactive T cells) T cells.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

---

What is claimed:

1. A method to treat a mammal that has cancer, said method comprising administering to said mammal a therapeutic composition comprising:

(a) a liposome delivery vehicle; and (b) a recombinant construct comprising a first isolated nucleic acid sequence encoding a superantigen, and a second isolated nucleic acid sequence encoding a cytokine, said first and second nucleic acid sequences being operatively linked to one or more transcription control sequences;

wherein said first and said second nucleic acid sequences encoding said superantigen and said cytokine, respectively, are coexpressed at or adjacent to said cancer; and wherein coexpression of said superantigen and said cytokine produces a result selected from the group consisting of alleviation of said cancer, reduction of a tumor associated with said cancer, elimination of a tumor associated with said cancer, prevention of meta static cancer, and stimulation of effector cell immunity against said cancer.

2. A method to treat a mammal that has cancer, said method comprising administering to said mammal a therapeutic composition comprising:

(a) a liposome delivery vehicle;

(b) a first recombinant construct comprising an isolated nucleic acid sequence encoding a superantigen operatively linked to one or more transcription control sequences; and (c) a second recombinant construct comprising an isolated nucleic acid sequence encoding a cytokine operatively linked to one or more transcription control sequences;

wherein said nucleic acid sequences encoding said superantigen and said cytokine, respectively, are coexpressed at or adjacent to said cancer; and wherein coexpression of said superantigen and said cytokine produces a result selected from the group consisting of alleviation of said cancer, reduction of a tumor associated with said cancer, elimination of a tumor associated with said cancer, prevention of metastatic cancer, and stimulation of effector cell immunity against said cancer.

3. A method to treat a mammal that has cancer, said method comprising:

(a) removing cells of said mammal;

(b) transfecting said cells in vitro with a recombinant construct comprising a first isolated nucleic acid sequence encoding a superantigen, and a second isolated nucleic acid sequence encoding a cytokine, said first and second nucleic acid sequences being operatively linked to one or more transcription control sequences; and (c) reintroducing said transfected cells to said mammal;

wherein said first and said second nucleic acid sequences encoding said superantigen and said cytokine, respectively, are coexpressed at or adjacent to said cancer; and wherein coexpression of said superantigen and said cytokine produces a result selected from the group consisting of alleviation of said cancer, reduction of a tumor associated with said cancer, elimination of a tumor associated with said cancer, prevention of metastatic cancer, and stimulation of effector cell immunity against said cancer.

4. A method to treat a mammal that has cancer, said method comprising:

(a) removing cells of said mammal;

(b) transletting said cells in vitro with a therapeutic composition comprising:

(i) a first recombinant construct comprising an isolated nucleic acid sequence encoding a superantigen operatively linked to one or more transcription control sequences; and (ii) a second recombinant construct comprising an isolated nucleic acid sequence encoding a cytokine operatively linked to one or more transcription control sequences; and (c) reintroducing said transfected cells to said mammal;

wherein said nucleic acid sequences encoding said superantigen and said cytokine, respectively, are coexpressed at or adjacent to said cancer; and wherein coexpression of said superantigen and said cytokine produces a result selected from the group consisting of alleviation of said cancer, reduction of a tumor associated with said cancer, elimination of a tumor associated with said cancer, prevention of metastatic cancer, and stimulation of effector cell immunity against said cancer.

5. The method of claim 1, 2, 3 or 4, wherein said superantigen is selected from the group consisting of staphylococcal enterotoxins, retroviral antigens, streptococcal antigens, mycoplasma antigens, mycobacteria antigens, viral antigens and protozoan antigens.

6. The method of claim 1, 2, 3 or 4, wherein said superantigen comprises staphylococcal enterotoxins.

7. The method of claim 1, 2, 3 or 4, wherein said superantigen is selected from the group consisting of SEA, SEB, $SEC_1$, $SEC_2$, $SEC_3$, SED, SEE and TSST.

8. The method of claim 1, 2, 3 or 4, wherein said superantigen is from a virus selected from the group consisting of mouse mammary tumor virus, rabies virus and herpes virus.

9. The method of claim 1, 2, 3 or 4, wherein said cytokine is selected from the group consisting of hematopoietic growth factors, interleukins, interferons, immunoglobulin superfamily molecules, tumor necrosis factor family molecules and chemokines.

10. The method of claim 1, 2, 3 or 4, wherein said cytokine is selected from the group consisting of granulocyte macrophage colony stimulating factor, macrophage colony stimulating factor, tumor necrosis factor α, interleukin-1, interleukin-6 and interleukin-12.

11. The method of claim 1, 2, 3 or 4, wherein said cytokine is selected from the group consisting of granulocyte macrophage colony stimulating factor and tumor necrosis factor.

12. The method of claim 1, 2, 3 or 4, wherein said cytokine comprises granulocyte macrophage colony stimulating factor.

13. The method of claim 1, 2, 3 or 4, wherein said transcription control sequences are selected from the group consisting of RSV control sequences, CMV control sequences, retroviral LTR sequences, SV-40 control sequences and β-actin control sequences.

14. The method of claim 2 or 4, wherein said first recombinant construct is selected from the group consisting of $PCR_3$-SEB, $PCR_3$-SEA, $PCR_3$-SEB.S, $PCR_3$-SEA.S, $PCR_3$-TSST and wherein said second recombinant construct is $PCR_3$-$GM_3$.

15. The method of claim 1 or 2, wherein said liposome delivery vehicle includes a compound capable of specifically delivering said liposome to said cancer.

16. The method of claim 1 or 2, wherein said therapeutic composition is administered to said mammal at or adjacent to said cancer.

17. The method of claim 1, 2, 3 or 4, wherein said mammal is a human.

18. The method of claim 1, 2, 3 or 4, wherein said mammal is selected from the from the group consisting of humans, dogs, cats, sheep, cattle, horses and pigs.

19. The method of claim 1, 2, 3 or 4, wherein said cancer is selected from the group consisting of melanomas, squamous cell carcinoma, breast cancers, head and neck carcinomas, thyroid carcinomas, soft tissue sarcomas, bone sarcomas, te sticular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, and hematopoietic neoplasias.

20. The method of claim 1, 2, 3 or 4, wherein said cancer is selected from the group consisting of melanomas, lung cancers, thyroid carcinomas, breast cancers, renal cell carcinomas, squamous cell carcinomas, brain tumors and skin cancers.

21. The method of claim 1, 2, 3 or 4, wherein said cytokine is an interleukin.

22. The method of claim 21, wherein said interleukin is selected from the group consisting of interleukin-1 (IL-1), interleukin-6 (IL-6) and interleukin-12 (IL-12).

23. The method of claim 22, wherein said interleukin is selected from the group consisting of interleukin-1 (IL-1), interleukin-6 (IL-6) and interleukin-12 (IL-12).

24. A method for increasing effector cell immunity against a cancer in a mammal, said method comprising administering to said mammal a therapeutic composition comprising:

(a) a liposome delivery vehicle; and (b) a recombinant construct comprising a first isolated nucleic acid sequence encoding a superantigen; and a second isolated nucleic acid sequence encoding a cytokine, said first and second nucleic acid sequences being operatively linked to one or more transcription control sequences;

wherein said first and said second nucleic acid sequences encoding said superantigen and said cytokine, respectively, are coexpressed at or adjacent to said cancer; and wherein coexpression of said superantigen and said cytokine results in an increase in effector immunity against said cancer.

25. A method for increasing effector cell immunity against a cancer in a mammal, said method comprising administering to said mammal a therapeutic composition comprising:

(a) a liposome delivery vehicle;

(b) a first recombinant construct comprising an isolated nucleic acid sequence encoding a superantigen operatively linked to one or more transcription control sequences; and (c) a second recombinant construct comprising an isolated nucleic acid sequence encoding a cytokine operatively linked to one or more transcription control sequences;

wherein said nucleic acid sequences encoding said superantigen and said cytokine, respectively, are coexpressed at or adjacent to said cancer; and wherein coexpression of said superantigen and said cytokine results in an increase in effector immunity against said cancer.

26. A method for increasing effector cell immunity against a cancer in a mammal, said method comprising:

(a) removing cells of said mammal;

(b) transfecting said cells in vitro with a recombinant construct comprising a first isolated nucleic acid sequence encoding a superantigen, and a second isolated nucleic acid sequence encoding a cytokine, said first and second nucleic acid sequences being operatively linked to one or more transcription control sequences; and (c) reintroducing said transfected cells to said mammal;

wherein said first and said second nucleic acid sequences encoding said superantigen and said cytokine, respectively, are coexpressed at or adjacent to said cancer; and wherein coexpression of said superantigen and said cytokine results in an increase in effector immunity against said cancer.

27. A method for increasing effector cell immunity against a cancer in a mammal, said method comprising:

(a) removing cells of said mammal;

(b) transfecting said cells in vitro with a therapeutic composition comprising:

(i) a first recombinant construct comprising an isolated nucleic acid sequence encoding a superantigen operatively linked to one or more transcription control sequences; and (ii) a second recombinant construct comprising an isolated nucleic acid sequence encoding a cytokine operatively linked to one or more transcription control sequences; and (c) reintroducing said transfected cells to said mammal;

wherein said nucleic acid sequences encoding said superantigen and said cytokine, respectively, are coexpressed at or adjacent to said cancer; and wherein coexpression of said superantigen and said cytokine results in an increase in effector immunity against said cancer.

28. A composition comprising a recombinant construct comprising a first isolated nucleic acid sequence encoding a superantigen and a second isolated nucleic acid sequence encoding a cytokine, wherein said isolated nucleic acid sequences are operatively linked to one or more transcription control sequences.

29. A composition comprising:

(a) a first recombinant construct comprising an isolated nucleic acid sequence encoding a superantigen operatively linked to one or more transcription control sequences; and (b) a second recombinant construct comprising an isolated nucleic acid sequence encoding a cytokine operatively linked to one or more transcription control sequences.

30. The composition of claim 28 or 29, wherein said composition further comprises a pharmaceutically acceptable carrier.

31. The composition of claim 30, wherein said pharmaceutically acceptable carrier is selected from the group consisting of an aqueous physiologically balanced solution, an artificial lipid-containing substrate, a natural lipid-containing substrate, an oil, an ester, a glycol, a virus and metal particles.

32. The composition of claim 30, wherein said pharmaceutically acceptable carrier comprises a delivery vehicle that delivers said nucleic acid sequences to a cancer in a mammal.

33. The composition of claim 32, wherein said delivery vehicle is selected from the group consisting of liposomes, micelles, and cells.

34. The composition of claim 32, wherein said delivery vehicle comprises a liposome.

35. The composition of claim 28 or 29, wherein said superantigen is selected from the group consisting of staphylococcal enterotoxins, retroviral antigens, streptococcal antigens, mycoplasma antigens, mycobacteria antigens, virus antigens and protozoan antigens.

36. The composition of claim 28 or 29, wherein said superantigen comprises staphylococcal enterotoxins.

37. The composition of claim 28 or 29, wherein said superantigen is selected from the group consisting of SEA, SEB, $SEC_1$, $SEC_2$, $SEC_3$, SED, SEE and TSST.

38. The composition of claim 28 or 29, wherein said superantigen is from a virus selected from the group consisting of mouse mammary tumor virus, rabies virus and herpes virus.

39. The composition of claim 28 or 29, wherein said cytokine is selected from the group consisting of hematopoietic growth factors, interleukins, interferons, immunoglobulin superfamily molecules, tumor necrosis factor family molecules and chemokines.

40. The composition of claim 28 or 29, wherein said cytokine is selected from the group consisting of granulocyte macrophage colony stimulating factor, macrophage colony stimulating factor, tumor necrosis factor α, interleukin-1, interleukin-6 and interleukin-12.

41. The composition of claim 28 or 29, wherein said cytokine is granulocyte macrophage colony stimulating factor and tumor necrosis factor α.

42. The composition of claim 28 or 29, wherein said transcription control sequences are selected from the group consisting of KSV control sequences, CMV control sequences, retroviral LTR control sequences, SV-40 control sequences and β-actin control sequences.

43. The composition of claim 29, wherein said first recombinant construct is selected from the group consisting of $PCR_3$-SEB, $PCR_3$-SEA, $PCR_3$-SEB.S, $PCR_3$-SEA.S, $PCR_3$-TSST and wherein said second recombinant construct is $PCR_3$-$GM_3$.

44. The composition of claim 34, wherein said composition is useful for treating a cancer selected from the group consisting of melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, and hematopoietic neoplasias, such that treatment of said cancer produces a result selected from the group consisting of alleviation of said cancer, reduction of a tumor associated with said cancer, elimination of a tumor associated with said cancer, prevention of metastatic cancer, and stimulation of effector cell immunity against said cancer.

45. The composition of claim 34, wherein said composition is useful for treating a cancer selected from the group consisting of melanomas, lung cancers, thyroid carcinomas, breast cancers, renal cell carcinomas, squamous cell carcinomas, brain tumors and skin cancers such that treatment of said cancer produces a result selected from the group consisting of alleviation of said cancer, reduction of a tumor associated with said cancer, elimination of a tumor associated with said cancer, prevention of metastatic cancer, and stimulation of effector cell immunity against said cancer.

46. The therapeutic composition of claim 28 or 29, wherein said cytokine is an interleukin.

47. A recombinant construct comprising an isolated nucleic acid sequence encoding a superantigen and an isolated nucleic acid sequence encoding a cytokine, wherein said isolated nucleic acid sequences are operatively linked to one or more transcription control sequences.

48. The construct of claim 47, wherein said transcription control sequence is selected from the group consisting of RSV control sequences, CMV control sequences, retroviral LTR control sequences, SV-40 control sequences and β-actin control sequences.

49. The construct of claim 47, wherein said superantigen-encoding nucleic acid sequence encodes a toxin selected from the group consisting of staphylococcal enterotoxins, retroviral antigens, streptococcal antigens, mycoplasma antigens, mycobacteria antigens, virus antigens and protozoan antigens.

50. The construct of claim 47, wherein said superantigen-encoding nucleic acid sequence encodes a toxin selected from the group consisting of a SEA, SEB, $SEC_1$, $SEC_2$, $SEC_3$, SED, SEE and TSST gene.

51. The construct of claim 47, wherein said superantigen-encoding nucleic acid sequence lacks a bacterial leader sequence.

52. The composition of claim 32, wherein said delivery vehicle comprises DOTMA and DOPE.

* * * * *

UNITED STATES PATENT AND TRADEMARK OFFICE
CERTIFICATE OF CORRECTION

PATENT NO. : 5,705,151
DATED : January 6, 1998
INVENTOR(S) : Dow et al.

It is certified that error appears in the above-identified patent and that said Letters Patent is hereby corrected as shown below:

In Claim 1, line 57, after "wherein", insert --said--.
In Claim 1, line 61, delete "meta static" and insert --metastatic-- therefor.
In Claim 2, line 53, after "wherein", insert --said--. In
In Claim 3, line 8, after "wherein", insert --said--.
In Claim 4, line 18, delete "transletting" and insert --transfecting-- therefor.
In Claim 4, line 32, after "wherein", insert --said--.
In Claim 23, line 45, delete "22" and insert --46-- therefor.
In Claim 24, line 62, after "wherein", insert --said--.
In Claim 25, line 12, after "wherein", insert --said--.
In Claim 26, line 30, after "wherein", insert --said--.
In Claim 27, line 50, after "wherein", insert --said--.
In Claim 42, line 48, delete "KSV" and insert --RSV-- therefor.
In Claim 23, line 45, delete "method" and insert --composition-- therefor.
In Claim 46, line 14, delete "therapeutic".

Signed and Sealed this

Fifth Day of May, 1998

Attest:

BRUCE LEHMAN

Attesting Officer

Commissioner of Patents and Trademarks